United States Patent
Schwartz et al.

(10) Patent No.: US 9,381,382 B2
(45) Date of Patent: *Jul. 5, 2016

(54) COMPOSITION COMPRISING A PARTICULATE ZINC MATERIAL, A PYRITHIONE OR A POLYVALENT METAL SALT OF A PYRITHIONE AND A GEL NETWORK

(75) Inventors: James Robert Schwartz, West Chester, OH (US); Eric Scott Johnson, Hamilton, OH (US); Bonnie Theresa King, Alexandria, KY (US); Carl Hinz Margraf, III, Frankfurt am Main (DE); Gregory V. Tormos, Loveland, OH (US); David Thomas Warnke, Cincinnati, OH (US); Debora W. Chang, Mason, OH (US); David Scott Dunlop, Mason, OH (US); Kevin M. Labitzke, Fairfield, OH (US); Sandra Lou Murawski, Fairfield, OH (US); William Jeffrey Gore, Montgomery, OH (US); Theodore Jay Verbrugge, Reily, OH (US); Elizabeth Marie Marzonie Elsner, Portage, MI (US); Jennifer Elaine Hilvert, Cincinnati, OH (US); Yingkun Jin, Mason, OH (US); Brian Michael Hurley, Blanchester, OH (US); Teresa Cuasay Manuel, Wester Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 754 days.

This patent is subject to a terminal disclaimer.

(21) Appl. No.: 11/602,770

(22) Filed: Nov. 21, 2006

(65) Prior Publication Data
US 2007/0128147 A1    Jun. 7, 2007

Related U.S. Application Data

(63) Continuation-in-part of application No. 11/216,520, filed on Aug. 31, 2005, which is a continuation-in-part of application No. 11/100,648, filed on Apr. 7, 2005, now abandoned, which is a continuation-in-part of application No. 10/802,166, filed on Mar. 17, 2004, now Pat. No. 8,491,877, application No. 11/602,770, which is a continuation-in-part of application No. 11/228,770, filed on Sep. 16, 2005, now Pat. No. 8,349,301, which is a continuation-in-part of application No. 10/454,433, filed on Jun. 4, 2003, now Pat. No. 7,303,744.

(60) Provisional application No. 60/455,963, filed on Mar. 18, 2003, provisional application No. 60/385,641, filed on Jun. 4, 2002.

(51) Int. Cl.
*A61K 31/555* (2006.01)
*A61K 8/27* (2006.01)
*A61K 8/60* (2006.01)
(Continued)

(52) U.S. Cl.
CPC .............. *A61Q 5/006* (2013.01); *A61K 8/0295* (2013.01); *A61K 8/042* (2013.01); *A61K 8/27* (2013.01); *A61K 8/342* (2013.01); *A61K 8/361* (2013.01); *A61K 8/37* (2013.01); *A61K 8/375* (2013.01); *A61K 8/39* (2013.01); *A61K 8/416* (2013.01); *A61K 8/42* (2013.01); *A61K 8/463* (2013.01); *A61K 8/49* (2013.01); *A61K 8/4933* (2013.01); *A61K 8/60* (2013.01); *A61K 8/737* (2013.01); *A61K 31/555* (2013.01); *A61Q 5/00* (2013.01); *A61Q 5/02* (2013.01); *A61Q 5/12* (2013.01)

(58) Field of Classification Search
CPC ... A61K 31/555; A61K 8/0295; A61K 8/042; A61K 8/27; A61K 8/342; A61K 8/361; A61K 8/37; A61K 8/375; A61K 8/39; A61K 8/416; A61K 8/42; A61K 8/463; A61K 8/49; A61K 8/4933; A61K 8/60; A61K 8/73
See application file for complete search history.

(56) References Cited

U.S. PATENT DOCUMENTS 2,396,278 A    3/1946  Lind
2,438,091 A    3/1948  Lynch
(Continued)

FOREIGN PATENT DOCUMENTS

CN    1658830       8/2005
DE    10005162 A1   8/2001
(Continued)

OTHER PUBLICATIONS

Eccleston, GM. (Colloids and Surfaces A: Physicochemical and Engineering Aspects 1997, 123-124:169-182).*
(Continued)

*Primary Examiner* — Ernst V Arnold
(74) *Attorney, Agent, or Firm* — Linda M. Sivik

(57) ABSTRACT

The present invention relates to a composition comprising an effective amount of a particulate zinc material, an effective amount of a detersive surfactant including a surfactant with an anionic functional group, an effective amount of a pyrithione or a polyvalent metal salt of a pyrithione, a dispersed gel network phase comprising: i) at least about 0.05% of one or more fatty amphiphiles, by weight of said shampoo composition; ii) at least about 0.01% of one or more secondary surfactants, by weight of said shampoo composition; and iii) water; and at least about 20% of an aqueous carrier, by weight of said shampoo composition.

37 Claims, No Drawings

(51) Int. Cl.
  *A61K 8/49* (2006.01)
  *A61Q 5/00* (2006.01)
  *A61Q 5/02* (2006.01)
  *A61Q 5/12* (2006.01)
  *A61K 8/02* (2006.01)
  *A61K 8/04* (2006.01)
  *A61K 8/34* (2006.01)
  *A61K 8/36* (2006.01)
  *A61K 8/37* (2006.01)
  *A61K 8/39* (2006.01)
  *A61K 8/41* (2006.01)
  *A61K 8/42* (2006.01)
  *A61K 8/46* (2006.01)
  *A61K 8/73* (2006.01)

(56) References Cited

U.S. PATENT DOCUMENTS

| | | | |
|---|---|---|---|
| 2,486,921 | A | 11/1949 | Byerly |
| 2,486,922 | A | 11/1949 | Strain |
| 2,528,378 | A | 10/1950 | Mannheimer |
| 2,658,072 | A | 11/1953 | Kosmin |
| 2,694,668 | A | 11/1954 | Fricke |
| 2,788,847 | A | 3/1957 | Cislak |
| 2,798,053 | A | 7/1957 | Brown |
| 2,809,971 | A | 10/1957 | Bernstein et al. |
| 2,826,551 | A | 3/1958 | Geen |
| 3,152,046 | A | 10/1964 | Kapral |
| 3,155,591 | A | 11/1964 | Hilfer |
| 3,236,733 | A | 2/1966 | Karsten et al. |
| 3,332,880 | A | 7/1967 | Kessler |
| 3,589,999 | A | 6/1971 | McRae et al. |
| 3,590,035 | A | 6/1971 | Damico |
| 3,753,196 | A | 8/1973 | Kurtz |
| 3,761,418 | A | 9/1973 | Parran |
| 3,773,770 | A | 11/1973 | Damico |
| 3,852,441 | A | 12/1974 | Kooistra, Jr. |
| 3,929,678 | A | 12/1975 | Laughlin |
| 3,940,482 | A | 2/1976 | Grand |
| 3,958,581 | A | 5/1976 | Abegg et al. |
| 3,959,461 | A | 5/1976 | Bailey |
| 3,960,782 | A | 6/1976 | Daley et al. |
| 3,964,500 | A | 6/1976 | Drakoff |
| 4,055,655 | A | 10/1977 | Maurer et al. |
| 4,089,945 | A | 5/1978 | Brinkman |
| 4,152,416 | A | 5/1979 | Spitzer |
| 4,161,526 | A | 7/1979 | Gorman |
| 4,197,865 | A | 4/1980 | Jacquet |
| 4,217,914 | A | 8/1980 | Jacquet |
| 4,235,873 | A | 11/1980 | Packman |
| 4,323,683 | A | 4/1982 | Bolich |
| 4,345,080 | A | 8/1982 | Bolich |
| 4,364,387 | A | 12/1982 | Larkin |
| 4,370,325 | A | 1/1983 | Packman |
| 4,379,753 | A | 4/1983 | Bolich |
| 4,381,919 | A | 5/1983 | Jacquet |
| 4,387,090 | A | 6/1983 | Bolich |
| 4,422,853 | A | 12/1983 | Jacquet |
| 4,470,982 | A | 9/1984 | Winkler |
| 4,507,280 | A | 3/1985 | Pohl |
| 4,529,586 | A | 7/1985 | De Marco |
| 4,608,183 | A | 8/1986 | Rossmoore |
| 4,654,213 | A | 3/1987 | Ramirez et al. |
| 4,663,158 | A | 5/1987 | Wolfram |
| 4,666,616 | A | 5/1987 | Rossmoore |
| 4,670,430 | A | 6/1987 | Imamura |
| 4,686,254 | A | 8/1987 | Lochhead |
| 4,704,272 | A | 11/1987 | Oh |
| 4,708,863 | A * | 11/1987 | Bews et al. ............... 424/47 |
| 4,788,006 | A | 11/1988 | Bolich |
| 4,834,767 | A | 5/1989 | Helioff |
| 4,885,107 | A | 12/1989 | Wetzel |
| 4,898,585 | A | 2/1990 | Borsanyi |
| 4,933,101 | A | 6/1990 | Cilley et al. |
| 4,943,432 | A | 7/1990 | Biener |
| 5,034,218 | A | 7/1991 | Duvel |
| 5,057,153 | A | 10/1991 | Ruggiero |
| 5,104,645 | A | 4/1992 | Cardin et al. |
| 5,104,646 | A | 4/1992 | Bolich |
| 5,106,609 | A | 4/1992 | Bolich |
| 5,106,613 | A | 4/1992 | Hartnett |
| 5,114,898 | A * | 5/1992 | Pinnavaia et al. ............ 502/406 |
| 5,120,831 | A | 6/1992 | Pickart |
| 5,202,048 | A | 4/1993 | Bartolo |
| 5,227,156 | A | 7/1993 | Wiese |
| 5,248,445 | A | 9/1993 | Rizvi |
| 5,284,649 | A | 2/1994 | Juneja |
| RE34,584 | E | 4/1994 | Grote |
| 5,358,667 | A | 10/1994 | Bergmann |
| 5,462,589 | A | 10/1995 | Nicholas |
| 5,466,425 | A * | 11/1995 | Adams ..................... 422/186.3 |
| 5,478,501 | A | 12/1995 | Rau |
| 5,518,774 | A | 5/1996 | Kappock et al. |
| 5,540,954 | A | 7/1996 | Nicholas |
| 5,562,995 | A | 10/1996 | Kappock |
| 5,580,494 | A | 12/1996 | Sandhu et al. |
| 5,614,538 | A | 3/1997 | Nelson, Jr. |
| 5,674,478 | A | 10/1997 | Dodd |
| 5,696,169 | A | 12/1997 | Arima et al. |
| 5,710,114 | A | 1/1998 | Pyles |
| 5,723,112 | A | 3/1998 | Bowser et al. |
| 5,726,137 | A | 3/1998 | Patel |
| 5,750,122 | A | 5/1998 | Evans |
| 5,756,076 | A | 5/1998 | Cervantes |
| 5,798,121 | A | 8/1998 | Cauwet et al. |
| 5,837,661 | A | 11/1998 | Evans |
| 5,853,707 | A | 12/1998 | Wells |
| 5,854,266 | A | 12/1998 | Nelson, Jr. |
| 5,854,319 | A | 12/1998 | O'Lenick |
| 5,874,476 | A | 2/1999 | Hsu |
| 5,876,705 | A | 3/1999 | Uchiyama |
| 5,880,076 | A | 3/1999 | Vermeer |
| 5,883,085 | A | 3/1999 | Blank et al. |
| 5,883,154 | A | 3/1999 | Kappock |
| 5,939,059 | A | 8/1999 | Franklin |
| 5,939,203 | A | 8/1999 | Kappock |
| 5,955,066 | A | 9/1999 | Sako et al. |
| 5,965,515 | A | 10/1999 | Rau |
| 6,017,562 | A | 1/2000 | Kaufman et al. |
| 6,034,043 | A | 3/2000 | Fujiwara |
| 6,303,109 | B1 | 10/2001 | Foerster |
| 6,309,628 | B1 | 10/2001 | Ansmann |
| 6,333,040 | B1 | 12/2001 | Boyxen |
| RE37,793 | E | 7/2002 | Domenico |
| 6,485,950 | B1 * | 11/2002 | Kumar et al. ............... 435/189 |
| 6,495,538 | B2 | 12/2002 | Fliss |
| 6,521,239 | B1 | 2/2003 | Breton et al. |
| 6,534,788 | B1 | 3/2003 | Yeo et al. |
| 6,649,585 | B1 | 11/2003 | Daute et al. |
| 6,719,967 | B1 | 4/2004 | Brown |
| 6,774,096 | B1 | 8/2004 | Paye |
| 6,780,913 | B2 | 8/2004 | Sawada et al. |
| 6,908,912 | B2 | 6/2005 | Rioux |
| 7,026,308 | B1 | 4/2006 | Gavin |
| 7,303,744 | B2 | 12/2007 | Wells et al. |
| 7,381,415 | B2 | 6/2008 | Yokoyama et al. |
| 7,674,785 | B2 | 3/2010 | Gavin et al. |
| 8,349,301 | B2 | 1/2013 | Wells |
| 8,349,302 | B2 | 1/2013 | Johnson et al. |
| 8,361,448 | B2 | 1/2013 | Johnson et al. |
| 8,361,449 | B2 | 1/2013 | Wells |
| 8,361,450 | B2 | 1/2013 | Johnson et al. |
| 8,367,048 | B2 | 2/2013 | Wells |
| 8,470,305 | B2 | 6/2013 | Johnson et al. |
| 2001/0047039 | A1 | 11/2001 | McManus |
| 2002/0012646 | A1 | 1/2002 | Royce |
| 2002/0119113 | A1 | 8/2002 | Ellis |
| 2002/0169283 | A1 | 11/2002 | Lu |
| 2003/0044471 | A1 | 3/2003 | Sakuma et al. |
| 2003/0095938 | A1 | 5/2003 | Casero |
| 2003/0119805 | A1 | 6/2003 | Fliss |
| 2003/0171231 | A1 | 9/2003 | Shana'a |
| 2003/0185779 | A1 | 10/2003 | Mitsumatsu |

(56) References Cited

U.S. PATENT DOCUMENTS

| | | |
|---|---|---|
| 2003/0215522 A1 | 11/2003 | Johnson |
| 2003/0223952 A1 | 12/2003 | Wells |
| 2003/0224955 A1 | 12/2003 | Ribery |
| 2004/0058855 A1 | 3/2004 | Schwartz |
| 2004/0167114 A1 | 8/2004 | Fliss |
| 2004/0191331 A1 | 9/2004 | Schwartz |
| 2004/0197294 A1 | 10/2004 | Seipel |
| 2004/0213751 A1 | 10/2004 | Schwartz |
| 2004/0223941 A1 | 11/2004 | Schwartz |
| 2004/0266886 A1 | 12/2004 | Seipel |
| 2005/0031569 A1 | 2/2005 | Seipel |
| 2005/0143268 A1 | 6/2005 | Midha |
| 2005/0181067 A1 | 8/2005 | Yokoyama |
| 2005/0202984 A1 | 9/2005 | Schwartz |
| 2006/0024256 A1 | 2/2006 | Wells |
| 2006/0024381 A1 | 2/2006 | Schwartz |
| 2006/0045861 A1 | 3/2006 | Bejger |
| 2006/0046943 A1 | 3/2006 | Erazo-Majewicz |
| 2006/0122573 A1 | 6/2006 | Terada et al. |
| 2007/0128147 A1 | 6/2007 | Schwartz et al. |
| 2012/0164198 A1 | 6/2012 | Johnson et al. |

FOREIGN PATENT DOCUMENTS

| | | |
|---|---|---|
| EP | 37318 A1 | 10/1981 |
| EP | 0077630 B1 | 4/1985 |
| EP | 1123693 A2 | 8/2001 |
| EP | 1145707 | 10/2001 |
| EP | 1161869 A | 12/2001 |
| FR | 2478467 | 9/1981 |
| FR | 2593801 A1 | 8/1987 |
| GB | 761171 | 11/1956 |
| GB | 849433 | 9/1960 |
| GB | 2141929 A | 1/1985 |
| GB | 2177108 A | 1/1987 |
| GB | 2230190 A | 10/1990 |
| JP | 52 092881 A | 8/1977 |
| JP | S60174707 | 2/1984 |
| JP | S61236708 | 4/1985 |
| JP | H06256689 | 12/1992 |
| JP | H0753369 | 8/1993 |
| JP | H07291615 | 4/1994 |
| JP | HEI 6-134227 | 5/1994 |
| JP | HEI 7-118103 | 5/1995 |
| JP | H10328280 | 12/1998 |
| JP | H10338521 | 12/1998 |
| JP | H11228368 | 8/1999 |
| JP | 200219607 | 8/2000 |
| JP | 2002515414 | 5/2002 |
| JP | 2002-104940 | 10/2002 |
| JP | 2005524690 | 3/2003 |
| JP | 2004-262805 A1 | 9/2004 |
| JP | 2006515331 | 9/2004 |
| JP | 2004-292387 A | 10/2004 |
| JP | 2004-292390 | 10/2004 |
| JP | 2004-307463 A | 11/2004 |
| JP | 2005-022983 A | 1/2005 |
| RO | RO87800 | 8/1983 |
| WO | WO93127559 | 3/1993 |
| WO | WO-93/08787 A2 | 5/1993 |
| WO | WO-94/10973 A1 | 5/1994 |
| WO | WO9534524 | 12/1995 |
| WO | WO9610387 | 4/1996 |
| WO | WO-96/25913 A | 8/1996 |
| WO | WO9806260 | 2/1998 |
| WO | WO-98/47372 A1 | 10/1998 |
| WO | WO9921568 | 5/1999 |
| WO | WO-99/51199 A1 | 10/1999 |
| WO | WO-99/59540 A1 | 11/1999 |
| WO | WO0006107 | 2/2000 |
| WO | WO-01/00149 A1 | 1/2001 |
| WO | WO0100021 | 1/2001 |
| WO | WO0100151 | 1/2001 |
| WO | WO-01/39735 A1 | 6/2001 |
| WO | WO0141727 | 6/2001 |
| WO | WO0151418 | 7/2001 |
| WO | WO0193817 | 12/2001 |
| WO | WO-02/32381 A2 | 4/2002 |
| WO | WO0230367 | 4/2002 |
| WO | WO-02/076422 A1 | 10/2002 |
| WO | WO-02/080943 A1 | 10/2002 |
| WO | WO03008957 | 1/2003 |
| WO | WO2006110385 | 10/2006 |
| WO | WO2006110386 | 10/2006 |

OTHER PUBLICATIONS

Saxton, Charles A. et al., "Antiplaque effects and mode of action of a combination of zinc citrate and a nonionic antimicrobial agent", *Scandinavian Journal of Dental Research*, Jun. 1988, vol. 96, No. 3, XP-001079620, Copenhagen, Denmark.

*Encyolopedia of Polymer Science and Engineering*, 1989, pp. 204-308, vol. 15, Second Edition, John Wiley & Sons, Inc.

D.J. Burgess, "Practical Analysis of Complex Coacervate Systems", *Journal of Colloid and Interface Science*, Nov. 1990, pp. 227-238, vol. 140, No. 1, Academic Press, Inc.

*CTFA Cosmetic Ingredient Dictionary*, 1982, 3$^{rd}$ Edition, The Cosmetic, Toiletry, and Fragrance Association, Inc., Washington, D.C. (book not enclosed).

Van Oss, C.J., "Coacervation, Complex-Coacervation and Flocculation", *J. Dispersion, Science and Technology*, 1989, pp. 581-573, vol. 9 (5,6), Marcel Dekker, Inc.

Noll, Walter, *Chemistry and Technology Silicones*, 1968, Academic Press, Inc., New York, NY. (book not enclosed).

McCutcheon, *Emulsifiers and Detergents*, 1989, MC Pub Co.(book not enclosed).

BASF, "Z-Cote microfine zinc oxide", XP-002287832, 2000, p. 1-7.

Van Cutsem, J. et al., XP-002288119, *Journal of the American Academy of Dermatology*, 1998, vol. 22, No. 61, p. 993-998, Amsterdam.

Akiyama, Hisanori et. al., "Effects of Zinc Oxide on the Attachment of *Staphylococcus aureus* Strains", Journal of Dermatological Science, 17 (1998) pp. 67-74.

Bennett, E.O. et al., "The Effects of Metals Upon the Inhibitory Activities of Cutting Fluid Preservatives", International Biodeterioration Bulletin, ISSN 0020-614 18(1) Spring 1982.

Khattar, M.M. and Salt, W.G., "Aspects of the Mode of Action of Pyrithione Against *Klebsiela pneumoniae*," Journal of Antimicrobial Chemotherapy, 1993, 5(S1), pp. 175-177.

Physical Characteristics of Minerals [online] downloaded from: http://dave.ucsc.edu/myrtreia/physical_character.html on Nov. 30, 2011; published Dec. 8, 2002; 4 pages).

Kravzov et al., "Relationship Between Physicochemical Properties of Prussian Blue and its Efficacy as Antidote Against Thallium Poisoning" Journal of Applied Toxicology, 1993, 13(3), 213-216.

Audebrand et al., "X-ray Diffraction Study of the Early Stages of the Growth of Nanscale Zinc Oxide Crystallites Obtained from Thermal Decomposition of Four Precursors. General Concepts on Precursor-Dependent Microstructural Properties" Chemistry of Materials, 1998, 10, 2450-2461.

McMurray, John, "Fats and Oils" Organic Chemistry, 2nd edition, Brooks-Cole Publishing Company, p. 1010 (1988).

MSDS Mallinckrodt Baker, Inc. Zinc Carbonate Feb. 16, 2006 pp. 1-7.

Making Matter, Layered Structures, Clays and Lubricants, 2 pages http://wwwold.ill.fr/dif/3D-crystals/layers.html.

International Search Report PCT/US2007/023772; Mail Date May 28, 2008 14 pages.

International Search Report PCT/US2006/012404; Mail Date Mar. 31, 2006 15 pages.

\* cited by examiner

COMPOSITION COMPRISING A PARTICULATE ZINC MATERIAL, A PYRITHIONE OR A POLYVALENT METAL SALT OF A PYRITHIONE AND A GEL NETWORK

CROSS REFERENCE TO RELATED APPLICATION

This application is a continuation-in-part of U.S. application Ser. No. 11/216,520, filed on Aug. 31, 2005, which is a continuation-in-part of U.S. application Ser. No. 11/100,648, filed on Apr. 7, 2005, which is a continuation-in-part of U.S. application Ser. No. 10/802,166, filed on Mar. 18, 2004, and claims the benefit of U.S. Provisional application Ser. No. 60/455,963, filed on Mar. 18, 2003. This application further claims the priority benefit and is a continuation in-part of U.S. application Ser. No. 11/228,770, filed on Sep. 16, 2005, which is a continuation-in part of prior co-pending U.S. application Ser. No. 10/454,433 filed on Jun. 4, 2003; which claims the benefit of U.S. Provisional Application Ser. No, 60/385, 641, filed on Jun. 4, 2002.

U.S. application Ser. No. 11/216,520, U.S. application Ser. No. 11/100,648, U.S. application Ser. No. 10/802,166, U.S. application Ser. No. 11/228,770, U.S. application Ser. No. 10/454,433 are all hereby incorporated herein by reference.

FIELD

The present invention relates to a composition comprising an effective amount of a particulate zinc material, a surfactant with an anionic functional group, an effective amount of a pyrithione or a polyvalent metal salt of a pyrithione and a gel network comprising a fatty amphiphile. More particularly, the present invention relates to personal care compositions and methods for the treatment of dandruff and compositions, which provide improved anti-dandruff activity.

BACKGROUND

Of the trace metals, zinc is the second most abundant metal in the human body, catalyzing nearly every bio-process directly or indirectly through inclusion in many different metalloenzymes. The critical role zinc plays can be discerned from the symptoms of dietary deficiency, which include dermatitis, anorexia, alopecia and impaired overall growth. Zinc appears especially important to skin health and has been used (typically in the form of zinc oxide or calamine) for over 3000 years to control a variety of skin problems. Recent data more specifically points to the healing and repairing properties of topical zinc treatment to damaged skin, often resulting in increased rates of healing. There is a growing body of biochemical support for this phenomenon. Since dandruff has been previously shown to represent significant damage to scalp skin, topical zinc treatment could aid in the repair process.

Inorganic salts, such as zinc hydroxycarbonate and zinc oxide, have been employed as bacteriostatic and/or fungistatic compounds in a large variety of products including paints, coatings and antiseptics. However, zinc salts do not possess as high of a level of biocidal efficacy as might be desired for many anti-dandruff and skin care applications.

Despite the options available, consumers still desire a shampoo that provides superior anti-dandruff efficacy along with improved conditioning benefit for dry hair, while not interfering with the cleansing or anti-dandruff efficacy, nor providing negative feel to the hair when it is dried. Such a combination can be difficult.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product.

In order to provide hair conditioning benefits in a cleansing shampoo base, a wide variety of conditioning actives have been proposed. However, many of these actives have the disadvantage of leaving the hair feeling soiled or coated and of interfering with the cleansing efficacy of the shampoo.

Coacervate formation in a shampoo composition is known to be advantageous for providing conditioning benefits to the hair. The use of cationic polymers to form coacervate is known in the art, such as in PCT publications WO 93/08787 and WO 95/01152. However, these shampoo compositions are good for delivering wet hair conditioning but are not capable of delivering satisfactory dry hair clean/smooth feel.

Based on the foregoing, there is a need for a conditioning shampoo which can provide improved conditioning benefit for dry hair, while not interfering with the cleansing efficacy, nor providing negative feel to the hair when it is dried. Specifically, there is a need for a shampoo which provides superior anti-dandruff efficacy and further provides long lasting moisturized feel, clean/smooth feel, and manageability control to the hair when the hair is dried, yet not leave the hair feeling greasy, as well as to provide softness and ease of combing when the hair is wet.

None of the existing art provides all of the advantages and benefits of the present invention.

SUMMARY

An embodiment of the present invention is directed to a composition comprising an effective amount of a particulate zinc material, an effective amount of a detersive surfactant including a surfactant with an anionic functional group, an effective amount of a pyrithione or a polyvalent metal salt of a pyrithione; a dispersed gel network phase comprising: i) at least about 0.05% of one or more fatty amphiphiles, by weight of said shampoo composition; ii) at least about 0.01% of one or more secondary surfactants, by weight of said shampoo composition; and iii) water; and at least about 20% of an aqueous carrier, by weight of said shampoo composition.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

It has now surprisingly been found, in accordance with the present invention, that anti-dandruff efficacy can be dramatically increased in topical compositions by the combination of an effective amount of a particulate zinc material with a surfactant with an anionic functional group and such topical compositions can further provide provides long lasting moisturized feel, clean/smooth feel, and manageability control to the hair when the hair is dried, by the use of a gel network in such topical compositions.

In an embodiment of the present invention, the particulate zinc material has a specified zinc lability within a surfactant system. Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Labile zinc is maintained by choice of an effective particulate zinc material or formation of an effective particulate zinc material in-situ by known methods.

It has now surprisingly been found, in accordance with the present invention, that anti-dandruff efficacy can be dramatically increased in topical compositions by the use of polyvalent metal salts of pyrithione, such as zinc pyrithione, in combination with particulate zinc materials, and further provide improved conditioning benefits by comprising a gel network. Therefore an embodiment of the present invention provides topical compositions with improved benefits to the skin and scalp (e.g., improved antidandruff efficacy and improved conditioning).

An embodiment of the present invention provides a stable composition for particulate zinc material dispersion where the zinc source resides in a particulate form. It has been shown to be challenging to formulate aqueous systems containing a particulate zinc material, due to the particulate zinc material's unique physical and chemical properties. Particulate zinc material may have a high density (approximately 3 g/cm$^3$), and needs to be evenly dispersed throughout the product and so it will not aggregate or settle. Particulate zinc material also has a very-reactive surface chemistry as well as the propensity to dissolve in systems with pH values below 6.5. Further, it has been surprisingly found that the particulate zinc material will remain labile, in the presence of a surfactant with an anionic functional group.

A particulate zinc material with a solubility of less than 25% will have a measurable % soluble zinc value below a threshold value determined by the weight percent and molecular weight of the zinc compound. The theoretical threshold value can be calculated by the following equation:

$$\frac{0.25 * wt. \% \text{ Zn Compound in Composition} * \text{moles of Zinc in Compound} * 65.39 \text{ (MW of Zn)}}{\text{MW of Zn Compound}}$$

An embodiment of the present invention is directed to a composition comprising an effective amount of a particulate zinc material having a aqueous solubility of less than about 25% by weight at 25° C.; an effective amount of a surfactant including a detersive surfactant with an anionic functional group; an effective amount of a pyrithione or a polyvalent metal salt of a pyrithione; a dispersed gel network phase comprising: i) at least about 0.05% of one or more fatty amphiphiles, by weight of said shampoo composition; ii) at least about 0.01% of one or more secondary surfactants, by weight of said shampoo composition; and iii) water; and at least about 20% of an aqueous carrier, by weight of said shampoo composition further wherein the pH of the composition is greater than about 6.5.

These, and other benefits, will become readily apparent from the detailed description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The components and/or steps, including those, which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more"

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "charge density", as used herein, refers to the ratio of the number of positive charges on a polymer to the molecular weight of said polymer.

The term "polymer" as used herein shall include materials whether made by polymerization of one type of monomer or made by two (i.e., copolymers) or more types of monomers.

The term "shampoo" as used herein means a composition for cleansing and conditioning hair or skin, including scalp, face, and body.

The term "suitable for application to human hair" as used herein means that the compositions or components thereof so described are suitable for use in contact with human hair and the scalp and skin without undue toxicity, incompatibility, instability, allergic response, and the like.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The shampoo compositions of the present invention comprise one or more detersive surfactants, a particulate zinc material, a pyrithione or a polyvalent metal salt of a pyrithione, a dispersed gel network phase, and an aqueous carrier. Each of these essential components, as well as preferred or optional components, is described in detail hereinafter.

A. Particulate Zinc Material

The composition of the present invention includes an effective amount of a particulate zinc material. Preferred embodiments of the present invention include from about 0.001% to about 10% of a particulate zinc layered material; more preferably from about 0.01% to about 7%; more preferably still from about 0.1% to about 5%.

Particulate zinc materials (PZM's) are zinc-containing materials which remain mostly insoluble within formulated compositions. Many benefits of PZM's require the zinc ion to be chemically available without being soluble, this is termed zinc lability. Physical properties of the particulate material have the potential to impact lability. We have discovered several factors which impact zinc lability and therefore have led to development of more effective formulas based on PZM's.

Particle physical properties which have been found to be important to optimize zinc lability of PZM's are morphology of the particle, surface area, crystallinity, bulk density, surface charge, refractive index, and purity level and mixtures thereof. Control of these physical properties has been shown to increase product performance.

Examples of particulate zinc materials useful in certain embodiments of the present invention include the following:

Inorganic Materials:

Zinc aluminate, Zinc carbonate, Zinc oxide and materials containing zinc oxide (i.e., calamine), Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide and hydroxy sulfate, zinc-containing layered materials and combinations thereof.

Further, layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLM's) may have zinc incorporated in the layers and/or as more labile components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-x}M^{3+}_x(OH)_2]^{x+}A^{m-}_{x/m} \cdot nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of ZLM's can be prepared called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1+x}(OH)_{3(1-y)}]^+A^{n-}_{(1=3y)/n} \cdot nH_2O$ where the two metal ion may be different; if they are the same and represented by zinc, the formula simplifies to $[Zn_{1+x}(OH)_2]^{2x+}2xA^- \cdot nH_2O$. This latter formula represents (where x=0.4) common materials such as zinc hydroxychloride and zinc hydroxynitrate. These are related to hydrozincite as well wherein the divalent anion is replaced by a monovalent anion. These materials can also be formed in situ in a composition or in or during a production process.

These classes of ZLM's represent relatively common examples of the general category and are not intended to be limiting as to the broader scope of materials which fit this definition.

Natural Zinc Containing Materials/Ores and Minerals:

Sphalerite (zinc blende), Wurtzite, Smithsonite, Franklinite, Zincite, Willemite, Troostite, Hemimorphite and combinations thereof.

Organic Salts:

Zinc fatty acid salts (i.e., caproate, laurate, oleate, stearate, etc.), Zinc salts of alkyl sulfonic acids, Zinc naphthenate, Zinc tartrate, Zinc tannate, Zinc phytate, Zinc monoglycerolate, Zinc allantoinate, Zinc urate, Zinc amino acid salts (i.e., methionate, phenylalinate, tryptophanate, cysteinate, etc) and combinations thereof.

Polymeric Salts:

Zinc polycarboxylates (i.e., polyacrylate), Zinc polysulfate and combinations thereof.

Physically Adsorbed Forms:

Zinc-loaded ion exchange resins, Zinc adsorbed on particle surfaces, Composite particles in which zinc salts are incorporated, (i.e., as core/shell or aggregate morphologies) and combinations thereof.

Zinc Salts:

zinc oxalate, zinc tannate, zinc tartrate, zinc citrate, zinc oxide, zinc carbonate, zinc hydroxide, zinc oleate, zinc phosphate, zinc silicate, zinc stearate, zinc sulfide, zinc undecylate, and the like, and mixtures thereof, preferably zinc oxide or zinc carbonate basic.

Commercially available sources of zinc oxide include Z-Cote and Z-Cote HPI (BASF), and USP I and USP II (Zinc Corporation of America).

Commercially available sources of zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Particle Size of PZM

In an embodiment of the present invention, it is has been found that a smaller particle size is inversely proportional to relative zinc lability. In an embodiment of the present invention, the particulate zinc material may have a particle size distribution wherein 90% of the particles are less than about 50 microns.

Surface Area of PZM

In an embodiment of the present invention, there may be a direct relationship between surface area and relative zinc lability. Increased particle surface area generally increases zinc lability due to kinetic factors. Particulate surface area can be increased by decreasing particle size and/or altering the particle morphology to result in a porous particle or one whose overall shape deviates geometrically from sphericity. In an embodiment of the present invention, the basic zinc carbonate may have a surface area of greater than about 10 $m^2/gm$.

Zinc Binding Materials

Materials which have a high affinity for zinc and have the tendency to result in the formation of insoluble complexes of zinc can foul the surface of particulate zinc materials (PZM's). By "fouling" it is meant the formation of an insoluble surface layer of the zinc binding material (ZBM) zinc salt which interferes with the kinetic lability of zinc from the base PZM material. The magnitude of negative effect of ZBM's is the product of the strength of association to zinc and the relative amount of the ZBM (relative to the PZM surface area). The PZM's can tolerate a portion of surface coverage without substantial inhibition of kinetic lability.

Those materials with high potential to bind to the PZM surface are ZBM's that form only sparingly soluble salts with zinc in water. "Sparingly soluble" refers to zinc salts with 1 gram (g)/100 g water solubility or less. These are the materials that form precipitated surface species on the PZM that interfere with zinc lability. Some non-limiting examples of zinc binding materials are laurate, citrate, valerate, oxalate, tartrate, iodate, thiocyanate, cyanide, sulfide, pyrophosphate, phosphate and mixtures thereof. A summary of the solubilities of common zinc salts and further disclosure of zinc biding material is found in U.S. application Ser. No. 11/216,520, filed Aug. 31, 2005 on pages 9-12 and incorporated by reference herein.

Many common raw materials may be sources for inadvertent ZBM's. In the case of fatty acids, for example, any material which originates from triglycerides or fatty acids will likely contain some level of fatty acid ZBM in the raw material as used.

Maximization of zinc lability from PZM's requires either complete avoidance of the presence of ZBM's or limiting the amount of the material to avoid complete coverage of the surface area of the PZM (i.e., saturation). An approximation of the amount of ZBM required to completely cover a PZM can be calculated based on effective surface area of the PZM and a knowledge of how tightly the ZBM can pack on the surface. The following example is illustrative of the process of approximating how much ZBM is certain to saturate and foul the entire PZM surface. It will be calculated for the general case in which a ZBM packs on the surface in a manner analogous to a surfactant adsorbing at an oil-water interface. In this case, a common value for surface area occupied per molecule is 30 Å$^2$ (equivalent to $3 \times 10^{-7} \mu^2$). It will be calculated per gram of a PZM with a measured surface area (SA, in $m^2/g$):

$$\frac{1 \ m^2 ZBM}{g \ PZM \cdot SA \ PZM} \times \frac{ZBM \ \text{molecule}}{3 \times 10^{-7} \ \mu^2 ZBM} \times \left(\frac{1 \times 10^6 \ \mu \ ZBM}{m \ ZBM}\right)^2 \times$$

-continued
$$\frac{\text{mol} \ ZBM}{6.02 \times 10^{23} \text{molecules} \ ZBM} \times \frac{1 \times 10^6 \ \mu\text{mol} \ ZBM}{\text{mol} \ ZBM} =$$
$$5.5 \ \mu\text{mol} \ ZBM / g \ PZM\text{-}SA \ PZM$$

Thus, 5.5 micromoles of ZBM will saturate 1 g of a PZM with a surface area of 1 $m^2/g$. Therefore, for the present invention, it is desirable that the composition comprises less than 5.5 micromoles of a zinc binding material (ZBM) per gram (g) of a particulate zinc material (PZM)/per $m^2/g$ surface area of a particulate zinc material (PZM).

For an example of zinc carbonate (a PZM) with a surface area of 30 $m^2/g$ and laurate as the ZBM, the calculation then becomes:

$$\frac{30 \ m^2 ZC}{g ZC} \times \left(\frac{1 \times 10^6 \ \mu \ ZC}{m ZC}\right)^2 \times \frac{LA \ \text{molecule}}{3 \times 10^{-7} \ \mu^2} \times$$
$$\frac{\text{mole} \ LA}{6.02 \times 10^{23} \text{molecules} \ LA} \times \frac{200 \ g \ LA}{\text{mole} \ LA} = 0.03 \ g LA/g ZC$$

Thus, approximately 0.03 g of laurate would saturate and foul the surface of one gram of a zinc carbonate PZM with the specified surface area. Based on this type of analysis, other "fouling levels" can be established for the specific ZBM-PZM combination. However, this example provides an approximation of the range of levels that need to be controlled to assure zinc lability of the PZM.

More specifically, then, a formulation containing 1.6% of the zinc carbonate specified above would require a laurate level below 0.048% (480 ppm) to remain effective. This would represent the total laurate present, whether added directly or inadvertently entering a formula via other raw material additions. This level also assumes there are no other ZBM's present; if there are, each needs to be considered separately while maintaining a combined amount below surface saturation level.

B. Pyrithione or a Polyvalent Metal Salt of Pyrithione

In a preferred embodiment, the present may comprise pyrithione or a polyvalent metal salt of pyrithione. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"); more preferably ZPT in platelet particle form, wherein the particles have an average size of up to about 20 μm, preferably up to about 5 μm, more preferably up to about 2.5 μm.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

It is further contemplated that when ZPT is used as the anti-microbial particulate in the anti-microbial compositions herein, that an additional benefit of hair growth or re-growth may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

Preferred embodiments include from about 0.01% to about 5% of a pyrithione or polyvalent metal salt of a pyrithione; more preferably from about 0.1% to about 2%.

In embodiments having a particulate zinc material and a pyrithione or polyvalent metal salt of pyrithione, the ratio of particulate zinc material to pyrithione or a polyvalent metal salt of pyrithione is preferably from 5:100 to 10:1; more preferably from about 2:10 to 5:1; more preferably still from 1:2 to 3:1.

C. Topical Carrier

In a preferred embodiment, the composition of the present invention is in the form of a topical composition, which includes a topical carrier. Preferably, the topical carrier is selected from a broad range of traditional personal care carriers depending on the type of composition to be formed. By suitable selections of compatible carriers, it is contemplated that such a composition is prepared in the form of daily skin or hair products including conditioning treatments, cleansing products, such as hair and/or scalp shampoos, body washes, hand cleansers, water-less hand sanitizer/cleansers, facial cleansers and the like.

In a preferred embodiment, the carrier is water. Preferably the compositions of the present invention comprise from 40% to 95% water by weight of the composition; preferably from 50% to 85%, more preferably still from 60% to 80%.

D. Detersive Surfactant

The composition of the present invention includes a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 2% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1{-}SO_3{-}M]$ where $R^1$ is a straight or branched chain, saturated, aliphatic hydrocarbon radical having from about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions are the beta-alkyloxy alkane sulfonates. These surfactants conform to the formula

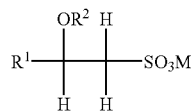

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is preferably sodium lauryl sulfate or sodium laureth sulfate.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

E. Dispersed Particles

The composition of the present invention may include additional dispersed particles. In the compositions of the present invention, it is preferable to incorporate at least 0.025% by weight of the dispersed particles, more preferably at least 0.05%, still more preferably at least 0.1%, even more preferably at least 0.25%, and yet more preferably at least 0.5% by weight of the dispersed particles. In one embodiment of the present invention, particles useful can be inorganic, synthetic, or semi-synthetic in origin. In the compositions of the present invention, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles F. Dispersed Gel Network Phase The shampoo compositions of the present invention comprise a dispersed gel network phase comprising a fatty amphiphile. The gel network phase is included in shampoo compositions of the present invention to provide conditioning benefits. As used herein, the term "gel network" refers to a lamellar or vesicular solid crystalline phase which comprises at least one fatty amphiphile as specified below, at least one secondary surfactant as specified below, and water or other suitable solvents. The lamellar or vesicular phase comprises bi-layers made up of a first layer comprising the fatty amphiphile and the secondary surfactant and alternating with a second layer comprising the water or other suitable solvent. The term "solid crystalline", as used herein, refers to the structure of the lamellar or vesicular phase which forms at a temperature below the chain melt temperature of the layer in the gel network comprising the one or more fatty amphiphiles, the chain melt temperature being at least about 27° C. The chain melt temperature may be measured by differential scanning calorimetry, a method of which is described in the Examples below.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol. 7*, 63-70 (1986).

In an embodiment of the present invention, the dispersed gel network phase is pre-formed. The term "pre-formed", as used herein, means that the mixture of the fatty amphiphile, secondary surfactant, and water or other suitable solvent is substantially a solid crystalline phase when added to the other components of the shampoo composition.

According to this embodiment of the present invention, the gel network component of the present invention is prepared as a separate pre-mix, which, after being cooled, is subsequently incorporated with the detersive surfactant and the other components of the shampoo composition. More specifically, the gel network component of the present invention may be prepared by heating the fatty amphiphile, the secondary surfactant, and water to a temperature of at least about 3 deg C. higher than the melting point of the highest melting-point material in the gel network phase, and mixing. This mixture is cooled to a level in the range of about 27° C. to about 35° C. by, for example, passing the mixture through a heat exchanger. As a result of this cooling step, the fatty amphiphile and the secondary surfactant crystallize to form a solid crystalline gel network.

Alternative methods of preparing the gel network component include sonication and/or milling of the fatty amphiphile, the secondary surfactant, and water, while these components are heated, to reduce the particle size of the melted fatty amphiphile phase. This results in an increase in surface area of the fatty amphiphile phase, which allows the secondary surfactant and the water to swell the fatty amphiphile phase. Another suitable variation in preparing the gel network includes heating and mixing the fatty amphiphile and the secondary surfactant first, and then adding that mixture to the water.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits. Further, the ELD does not form if the components which comprise the gel network component (i.e., the fatty amphiphile and the secondary surfactant combined with water) are added as individual components together with the other components of the shampoo composition in one mixing step, and not as a separate cooled pre-formed gel network component.

The presence of the gel network in the pre-mix and in the final shampoo composition in the form of the ELD can be confirmed by means known to one of skill in the art, such as X-ray analysis, optical microscopy, electron microscopy, and differential scanning calorimetry. Methods of X-ray analysis and differential scanning calorimetry are described in the Examples below.

In an embodiment of the present invention, the weight ratio of the fatty amphiphile to the secondary surfactant in the gel network component is greater than about 1:9, preferably greater than about 1:5 to about 100:1, more preferably greater than about 1:1 to about 50:1, and even more preferably greater than about 2:1 to about 10:1.

The shampoo composition of the present invention comprise a gel network in an amount greater than about 0.1%, preferably from about 1% to about 60%, and more preferably from about 5% to about 40%, by weight of the shampoo composition.

1. Fatty Amphiphile

The gel network component of the present invention comprises at least one fatty amphiphile. As used herein, "fatty amphiphile" refers to a compound having a hydrophobic tail group of $R_1$ as defined below and a hydrophilic head group which does not make the compound water soluble, wherein the compound also has a net neutral charge at the pH of the shampoo composition. The term "water soluble", as used herein, means that the material is soluble in water in the present composition. In general, the material should be soluble at 25° C. at a concentration of 0.1% by weight of the water solvent, preferably at 1%, more preferably at 5%, more preferably at 15%.

The fatty amphiphile of the present invention may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

The shampoo compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the shampoo composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

According to the present invention, suitable fatty amphiphiles have a hydrophobic tail group of $R_1$. As used herein, $R_1$ is an alkyl, alkenyl (containing up to 3 double bonds), alkyl aromatic, or branched alkyl group of $C_{12}$-$C_{70}$ length. Non-limiting examples of alkyl, alkenyl, or branched alkyl groups suitable for the fatty amphiphiles of the present invention include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

As used herein, $R_1$ also may be a branched alkyl group prepared by alkaline condensation of alcohols to give higher molecular weight, branched isoalcohols. These branched isoalcohols are referred to in the art as Guerbet alcohols.

$R_1$ may be alkyl, alkenyl or branched carbon chains of vegetable origin, such as wheat germ, sunflower, grape seed, sesame, maize, apricot, castor, avocado, olive, soybean, sweet almond, palm, rapeseed, cotton seed, hazelnut, macadamia, karite, jojoba, alfalfa, poppy, pumpkinseed, sesame, cucumber, blackcurrant, evening primrose, millet, barley, quinoa, rye, safflower, candlenut, passion flower or musk rose oil, and karite butter.

Suitable fatty amphiphiles of the present invention also have a hydrophilic head group which does not make the compound water soluble, such as in compounds having an HLB of 6 or less. Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids.

To form the gel network component of the present invention, individual fatty amphiphile compounds or combinations of two or more different fatty amphiphile compounds may be selected. The following provides non-limiting examples of classes of compounds from which one or more fatty amphiphiles suitable for use in the present invention may be selected.

a. Fatty Alcohols/Alkoxylated Fatty Alcohol Ethers

Fatty amphiphiles of the present invention may be selected from fatty alcohol compounds or alkoxylated fatty alcohol ether compounds according to the following formula:

wherein $R_1$ is as described above; $R_2$ is a $C_1$-$C_5$ carbon chain which may be branched or hydroxy substituted; and k is a number ranging from about 0 to about 5.

The fatty alcohols useful herein are those having from about 12 to about 60 carbon atoms, preferably from about 16 to about 60 carbon atoms. These fatty alcohols may be straight or branched chain alcohols and may be saturated or unsaturated. Non-limiting examples of suitable fatty alcohols include cetyl alcohol, stearyl alcohol, arachidyl alcohol, behenyl alcohol, C20-40 alcohols, C30-50 alcohols, C40-60 alcohols, and mixtures thereof.

Suitable alkoxylated fatty alcohol ethers include addition products of 1 to 5 mol of ethylene oxide with a linear fatty alcohol having about 12 to about 60 carbon atoms, which are all adducts obtainable by the known industrial oxyethylation processes. Also suitable are the polyethylene oxide condensates of alkyl phenols, for example, the condensation products of alkyl phenols having an alkyl group containing from about 12 to about 60 carbon atoms in either a straight chain or branched chain configuration, with ethylene oxide, wherein the ethylene oxide is present in amounts equal to from about 1 to about 5 moles of ethylene oxide per mole of alkyl phenol. Further suitable alkoxylated fatty alcohol ethers include those derived from the condensation of ethylene oxide with the product resulting from the reaction of propylene oxide and ethylene diamine products.

Non-limiting examples of suitable alkoxylated fatty alcohol ethers include steareth-2, beheneth-2, beheneth-5, beheneth-10, C20-40 Pareth-3, C20-40 Pareth-10, C30-50 Pareth-3, and C30-50-Pareth-10.

b. Di-Fatty Ethers

Fatty amphiphiles of the present invention may be selected from di-fatty ether compounds according to the following formula:

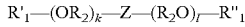

wherein $R_1$ is as described above; $R_2$ is a $C_1$-$C_5$ carbon chain which can be branched or hydroxy substituted; k and l each is independently a number such that the sum (k+l) has a value ranging from 1 to 30; and Z is an ether (i.e., —O—) or an amine (i.e., —$NR_2$—, wherein $R_2$ is as described immediately above).

Compounds of the above formula in which Z is an ether (i.e., dialkyl oxyethyl ethers) may be prepared by esterification processes, which are known in the art, of fatty alcohols and fatty alkyl oxyethanols. Compounds of the above formula in which Z is an amine group may be obtained, for example, from triethanolamine by O-alkylation with 2 mol of a sulfuric half-ester salt of a $C_{12}$-$C_{60}$ fatty alcohol, according to a process for the preparation of ether amines described in DE 35 04 242.

Non-limiting examples of suitable di-fatty ether compounds include dicetylstearyl ether, dicetylstearyl dioxyethyl ether, and N,N-bis(2-cetylstearyl-oxyethyl)aminoethanol.

c. Fatty Amides/Fatty Alkanolamides/Fatty Alkoxylated Amides

Fatty amphiphiles of the present invention also may be selected from fatty amide compounds according to the following formula:

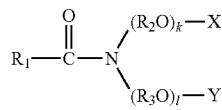

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y are each independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty amides, fatty alkanolamides or fatty alkoxylated amides are disclosed in U.S. application Ser. No. 11/228,770, filed Sep. 16, 2005 on pages 15-16 and incorporated by reference herein.

d. Fatty Carbamates

Fatty amphiphiles of the present invention may be selected from fatty carbamate compounds according to the following formula:

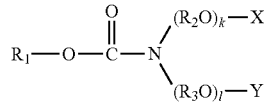

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty carbamates include cetyl carbamate, stearyl carbamate, PEG-2 stearyl carbamate, PEG-4 stearyl carbmate, and behenyl carbamate.

e. Fatty Alkylamido Alkylamines

Fatty amphiphiles of the present invention also may be selected from fatty alkylamido alkylamine compounds according to the following formula:

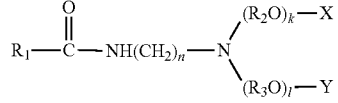

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage; and n is a number ranging from about 1 to about 4.

Non-limiting examples of suitable fatty alkylamido alkylamine compounds are disclosed in U.S. application Ser. No. 11/228,770, filed Sep. 16, 2005 on pages 16-17 and incorporated by reference herein.

f. Fatty Amines/Fatty Alkanolamines/Fatty Alkoxylated Amines

Fatty amphiphiles of the present invention further may be selected from fatty amine compounds according to the following formula:

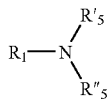

wherein $R_1$ is as described above; and $R'_5$ and $R''_5$ are independently hydrogen or a $C_1$-$C_5$ carbon chain which can be branched or hydroxy substituted.

Additionally, fatty amphiphiles of the present invention may be selected from fatty alkoxylated amine compounds according to either one of the following formulas:

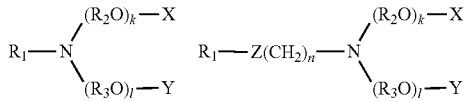

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via amide, ester, or ether linkage; n is a number ranging from about 1 to about 4; and Z is an ether (i.e., —O—) or an amine (i.e., —NH—).

Primary, secondary, and tertiary fatty amines are useful. Suitable fatty alkoxylated amine compounds include addition products of ethylene oxide with a linear fatty alkylamine having 12 to 60 carbon atoms, all of which are adducts obtainable by known industrial processes and which are commercially available.

Non-limiting examples of suitable fatty amine and fatty alkoxylated amine compounds are disclosed in U.S. application Ser. No. 11/228,770, filed Sep. 16, 2005 on pages 17-18 and incorporated by reference herein.

g. Fatty Amine Oxides

Fatty amphiphiles of the present invention also may be selected from fatty amine oxide compounds according to the following formula:

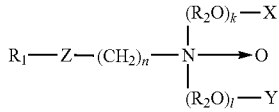

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via an amide, ester, or ether linkage; Z is an ether (i.e., —O—) or an amide (i.e., —C(O)—NH—) linkage; and n is a number ranging from about 1 to about 4. In accord with known convention, the arrow in the above formula is representative of a semi-polar bond.

Non-limiting examples of suitable amine oxide compounds include are disclosed in U.S. application Ser. No. 11/228,770, filed Sep. 16, 2005 on pages 18-19 and incorporated by reference herein.

h. Alkoxylated Fatty Acid

Fatty amphiphiles of the present invention also may be selected from fatty acid or alkoxylated fatty acid compounds according to the following formula:

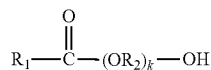

wherein $R_1$ is as described above; $R_2$ is a $C_1$-$C_5$ carbon chain which can be branched or hydroxy substituted; and k is a number ranging from about 1 to about 5.

Non-limiting examples of suitable alkoxylated fatty acids include PEG-8 behenate, PEG-5 cocoate, PEG-10 cocoate, PEG-2 laurate, PEG-4 laurate PEG-6 laurate, PEG-8 laurate, PEG-9 laurate, PEG-10 laurate, PEG-7 oleate, PEG-2 stearate, PEG-3 stearate, PEG-4 stearate, PEG-5 stearate, PEG-6 stearate, PEG-7 stearate, PEG-8 stearate, PEG-9 stearate, PEG-10 stearate, polyglyceryl-2-PEG-4 stearate, PPG-2 isostearate, and PPG-9 laurate.

i. Fatty Esters

Fatty amphiphiles of the present invention may be selected from fatty ester compounds according to the following formula:

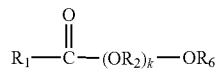

wherein $R_1$ is as described above; $R_2$ is a $C_1$-$C_5$ carbon chain which can be branched or hydroxy substituted; k is a number ranging from about 1 to about 5; and $R_6$ is a $C_1$-$C_{40}$ carbon chain or an alkylcarbonyl (i.e.,

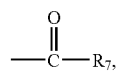

wherein $R_7$ is a $C_1$-$C_{40}$ carbon chain).

These suitable fatty esters include esters with hydrocarbyl chains derived from fatty acids or alcohols (e.g., mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Non-limiting examples of suitable fatty ester compounds are disclosed in U.S. application Ser. No. 11/228,770, filed Sep. 16, 2005 on pages 19-20 and incorporated by reference herein Fatty amphiphiles of the present invention also may be selected from other fatty ester compounds according to the following formula:

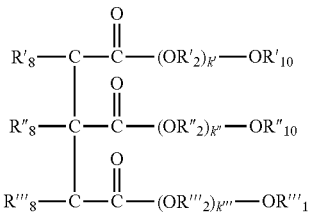

wherein $R'_8$, $R''_8$, and $R'''8$ each is independently selected from hydrogen, hydroxy, or a $C_1$-$C_4$ carbon chain which can be branched or hydroxy substituted; k', k", and k''' each is independently a number such that the sum (k'+k"+k''') has a value ranging from 0 to 15; $R'_2$, $R''_2$, and $R'''_2$ each is independently selected from a $C_1$-$C_5$ carbon chain which can be branched or hydroxy substituted; and where $R'_{10}$, $R''_{10}$, $R'''_{10}$ each is independently selected form hydrogen or $R_1$, where $R_1$ is as defined above, provided that at least one of $R'_{10}$, $R''_{10}$, and $R'''_{10}$ is a $R_1$ group.

Still other suitable fatty esters are di- and tri-alkyl and alkenyl esters of carboxylic acids, such as esters of $C_4$ to $C_8$ dicarboxylic acids (e.g., $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearoyl stearate, stearyl citrate, distearyl citrate and tristearyl citrate.

Fatty amphiphiles of the present invention further may be selected from other fatty ester compounds according to the following formula:

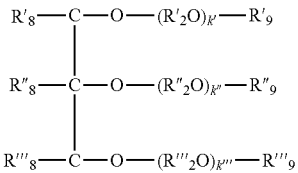

wherein $R'_2$, $R''_2$, and $R'''_2$ each is independently selected from a $C_1$-$C_5$ carbon chain which can be branched or hydroxy substituted; $R'_8$, $R''_8$, and $R'''8$ each is independently selected from hydrogen, hydroxy, or $C_1$-$C_4$ carbon chain which can be branched or hydroxy substituted; k', k", and k''' each is independently a number such that the sum (k'+k"+k''') has a value ranging from 0 to 15; and $R'_9$, $R''_9$, and $R'''9$ each is independently selected from hydrogen or alkylcarbonyl (i.e.,

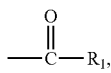

wherein $R_1$ is as described above), provided that at least one of $R'_9$, $R''_9$, and $R'''_9$ is a

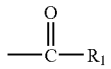

group.

Other suitable fatty esters are those known as polyhydric alcohol esters. Such polyhydric alcohol esters include those disclosed in U.S. application Ser. No. 11/228,770, filed Sep. 16, 2005 on page 21 and incorporated by reference herein.

Still other fatty esters suitable for use in the compositions of the present invention are glycerides, including, but not limited to, mono-, di-, and tri-glycerides, preferably mono- and di-glycerides, more preferably mono-glycerides. For use in the compositions described herein, the glycerides are preferably the mono-, di-, and tri-esters of glycerol and long chain carboxylic acids, such as $C_{12}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

j. Fatty Phosphorus Compounds

Fatty amphiphiles of the present invention may be selected from fatty phosphorus compounds according to the following formula:

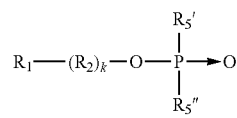

wherein $R_1$ is as described above; $R_2$ is a $C_1$-$C_5$ carbon chain which can be branched or hydroxy substituted; k is a number ranging from about 0 to about 5; and $R_5$ is hydrogen or a $C_1$-$C_4$ carbon chain which can be branched or hydroxy substituted. In accord with known convention, the arrow in the above formula is representative of a semi-polar bond.

Non-limiting examples of suitable fatty phosphorus compounds include those disclosed in U.S. application Ser. No. 11/228,770, filed Sep. 16, 2005 on page 22 and incorporated by reference herein.

k. Fatty Sorbitan Derivatives

Fatty amphiphiles of the present invention also may be selected from fatty sorbitan derivative compounds according to the following formula:

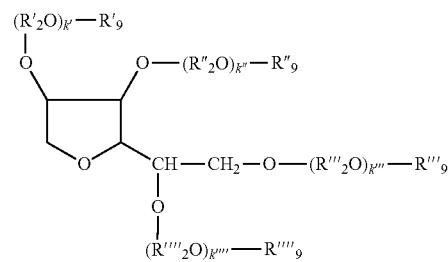

wherein $R'_2$, $R''_2$, $R'''_2$, and $R''''_2$ each is independently a $C_1$-$C_5$ carbon chain which can be branched or hydroxy substituted; $R'_9$, $R''_9$, $R'''_9$, and $R''''_9$ each is independently hydrogen or alkylcarbonyl (i.e.,

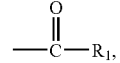

wherein $R_1$ is as described above), provided that at least one of $R'_9$, $R''_9$, $R'''_9$, and $R''''_9$ is a $$-\overset{\overset{\displaystyle O}{\|}}{C}-R_1$$

group; and k', k", k'", and k"" each is independently a number such that the sum (k'+k"+k'"+k"") has a value ranging from 0 to 20.

Non-limiting examples of suitable fatty sorbitan derivatives include those disclosed in U.S. application Ser. No. 11/228,770, filed Sep. 16, 2005 on pages 22-23 and incorporated by reference herein.

l. Sucrose Polyesters

Fatty amphiphiles of the present invention may be selected from sucrose polyester compounds according to the following formula:

wherein $R'_9$, $R''_9$, $R'''_9$, $R''''_9$, $R'''''_9$, $R''''''_9$, $R'''''''9$, and $R''''''''_9$ each is hydrogen or alkylcarbonyl (i.e., $$-\overset{\overset{\displaystyle O}{\|}}{C}-R_1,$$

wherein $R_1$ is as described above), provided that at least one of $R'_9$, $R''_9$, $R'''_9$, $R''''_9$, $R'''''_9$, $R''''''_9$, $R'''''''_9$, and $R''''''''_9$, is a $$-\overset{\overset{\displaystyle O}{\|}}{C}-R_1$$

group.

Non-limiting examples of suitable sucrose polyester compounds include those disclosed in U.S. application Ser. No. 11/228,770, filed Sep. 16, 2005 on pages 23-24 and incorporated by reference herein.

m. Alkyl Sulfoxides

Fatty amphiphiles of the present invention further may be selected from alkyl sulfoxide compounds according to the following formula:

$$R_1-\overset{\overset{\displaystyle (R_2O)_k-X}{|}}{S}\rightarrow O$$

wherein $R_1$ is as described above; $R_2$ is a $C_1$-$C_5$ carbon chain which can be branched or hydroxy substituted; k is a number ranging from about 0 to about 10; and X and Y each is independently selected from hydrogen or a $C_1$-$C_4$ carbon chain which can be branched or hydroxy substituted.

Non-limiting examples of suitable alkyl sulfoxide compounds include those disclosed in U.S. application Ser. No. 11/228,770, filed Sep. 16, 2005 on pages 24-25 and incorporated by reference herein.

2. Secondary Surfactant

The gel network component of the present invention also comprises a secondary surfactant. As used herein, "secondary surfactant" refers to one or more surfactants which are combined with the fatty amphiphile and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

The shampoo compositions of the present invention comprise secondary surfactant as part of the pre-formed dispersed gel network phase in an amount from about 0.01% to about 15%, preferably from about 0.1% to about 10%, and more preferably from about 0.3% to about 5%, by weight of the shampoo composition.

As described above, for use in the present invention, the weight ratio of the fatty amphiphile to the secondary surfactant is greater than about 1:9, preferably greater than about 1:5 to about 100:1, more preferably greater than about 1:1 to about 50:1, and even more preferably greater than about 2:1 to about 10:1.

Suitable secondary surfactants include anionic, zwitterionic, amphoteric, cationic, and nonionic surfactants as generally described above in the Detersive Surfactant section.

Preferred anionic surfactants for use as secondary surfactants of the present invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof.

Cationic surfactants suitable for use as secondary surfactants of the present invention include quaternary ammonium salts or amido-amines having at least one fatty chain containing at least about 8 carbon atoms and mixture thereof.

Suitable quaternary ammonium salts have the following general formula:

$$N^+(R_1R_2R_3R_4)X^-$$

wherein $R_1$ is selected from linear and branched radicals comprising from about 8 to about 12 carbon atoms; $R_2$ is selected from linear and branched radicals comprising from about 8 to 12 carbon atoms or the same group as radicals $R_3$ and $R_4$; $R_3$ and $R_4$ are independently selected from linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy, and alkylamide radicals; and X— is an anion selected from halides such as chloride, bromide, and iodide, ($C_2$-$C_6$) alkyl sulphates, such as methyl sulphate, phosphates, alkyl, and alkylaryl sulphonates, and anions derived from organic acids, such as acetate and lactate.

Non-limiting examples of such suitable cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, and mixtures thereof.

Suitable amido-amine cationic surfactants have the following general formula:

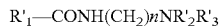

$R'_1$—CONH($CH_2$)$n$N$R'_2$$R'_3$ wherein $R'_1$ is selected from linear and branched radicals comprising about 8 to about 12 carbon atoms; $R'_2$ and $R'_3$ are independently selected from hydrogen, linear and branched aliphatic radicals comprising from about 1 to about 4 carbon atoms, and aromatic radicals such as aryl and alkylaryl, wherein the aliphatic radicals may comprise at least one hetero atom such as oxygen, nitrogen, sulphur, and halogens, and the aliphatic radicals are chosen, for example, from alkyl, alkoxy and alkylamide radicals; and n is an integer from about 1 to about 4.

Non-limiting examples of such suitable amido-amines include stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyldiethylamine, arachidamidoethyldiethylamine, arachidamidoethyldimethylamine, and mixtures thereof.

Suitable nonionic surfactants include nonionic surfactants having an HLB of 7 or more and comprising one or more polyethyleneoxide chains wherein each polyethyleneoxide chain contains on average at least about 5 ethylene oxide units.

Nonionic surfactants comprising one or more polyethyleneoxide chain wherein each polyethyleneoxide chain contains on average at least about 5 ethylene oxide units include polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, and polyethoxylated fatty amines, with a number of ethylene oxide groups of at least about 5, and mixtures thereof.

Among preferred nonionic surfactants comprising one or more polyethyleneoxide chain include polyoxyethylene alkyl ethers having at least about 5, preferably from about 10 to 20, ethylene oxide units. Examples of such nonionic surfactants are steareth-10 and steareth-15.

Also suitable for use as nonionic surfactants are nonionic surfactants having an HLB of 7 or more which are free of polyethyleneoxide chains. Nonionic surfactants free of polyethyleneoxide chains include polyglycerolated fatty acids, polyglycerolated fatty amides, polyglycerolated alkyl phenols, polyglycerolated α-diols, polyglycerolated alcohols, alkyl polyglucosides, and sugar esters. Preferably, suitable nonionic surfactants free of polyethyleneoxide chains are selected from alkyl polyglucosides, sugar esters, polyglyceryl fatty acid esters, alkyl polyglyceryl ethers, and mixtures thereof.

Suitable secondary surfactants of the present invention also include so-called gemini surfactants. Gemini surfactants are generally described by F. M. Menger and C. A. Littau, "Gemini Surfactants: A New Class of Self-Assembling Molecules", J. Am. Chem. Soc. 1993, 115, 10083-10090; and by B. S. Sekon, "Gemini (dimeric) Surfactants: The Two Faced Molecules", Resonance, 42-49 (March 2004). Examples of suitable gemini surfactants are described in U.S. Pat. Nos. 5,922,671; 6,204,297; 6,358,914; 6,710,022; 6,777,384; 6,794,345; and 6,797,687.

More than one surfactant of the above specified types may be used for the secondary surfactant of the present invention.

3. Water or Suitable Solvents

The gel network component of the present invention also comprises water or suitable solvents. The water or suitable solvent and the secondary surfactant together contribute to the swelling of the fatty amphiphile. This, in turn, leads to the formation and the stability of the gel network. As used herein, the term "suitable solvent" refers to any solvent which can be used in the place of or in combination with water in the formation of the gel network of the present invention.

The shampoo compositions of the present invention comprise water or suitable solvents as part of the pre-formed dispersed gel network phase in an amount suitable to achieve a gel network when combined with fatty amphiphile and secondary surfactant according to the present invention.

In a preferred embodiment, the shampoo compositions of the present invention comprise as part of the pre-formed dispersed gel network phase at least about 0.05% of water or a suitable solvent, by weight of the shampoo composition.

In another embodiment of the present invention, the shampoo compositions comprise water or a suitable solvent as part of the pre-formed dispersed gel network phase is an amount relative to the amount of fatty amphiphile at a weight ratio of at least about 1:1.

G. Aqueous Carrier

The compositions of the present invention are typically in the form of pourable liquids (under ambient conditions). The compositions will therefore typically comprise an aqueous carrier, which is present at least about 20% of an aqueous carrier, by weight of a shampoo composition, and in a further embodiment, an aqueous carrier is present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

H. Additional Components

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10%.

Non-limiting examples of optional components for use in the composition include cationic polymers, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins, minerals, herbal/fruit/food extracts, sphingolipids derivatives or synthetical derivative, and clay.

I. Deposition Aid

The shampoo compositions of the present invention may include a deposition aid. The deposition aid is included to effectively enhance deposition of the gel network component. The deposition aid can comprise any material that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, preferably from about 0.075% to about 2.5%, more preferably from about 0.1% to about 1.0%, by weight of the shampoo composition.

In one embodiment of the present invention, the deposition aid is a cationic polymer.

1. Cationic Polymers

The compositions of the present invention may contain a cationic polymer. Concentrations of the cationic polymer in the composition typically range from about 0.05% to about 3%, preferably from about 0.075% to about 2.0%, more preferably from about 0.1% to about 1.0%. Preferred cationic polymers will have cationic charge densities of at least about 0.4 meq/gm, preferably at least about 1.2 meq/gm, more preferably at least about 1.5 meq/gm, but also preferably less than about 7 meq/gm, more preferably less than about 5 meq/gm. Herein, "cationic charge density" of a polymer refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

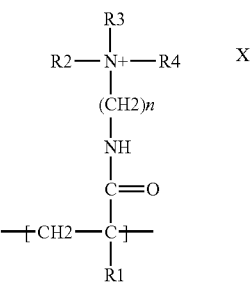

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

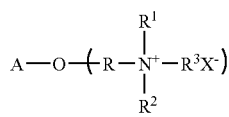

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962, 418. Other suitable cationic polymers include copolymers of etherified cellulose, guar and starch, some examples of which are described in U.S. Pat. No. 3,958,581. Guar is an example of one type of galactomannan polymer, specifically having a mannose to galactose ratio of 2 monomers of mannose to 1 monomer of galactose. Another suitable cationic polymer includes galactomannan polymer derivatives with a net positive charge and having a mannose to galactose ratio of greater than 2:1 on a monomer to monomer basis (i.e., non-guar galactomannan polymers). The gum for use in preparing the non-guar galactomannan polymer derivatives is typically obtained as naturally occurring material such as seeds or beans from plants. Examples of various non-guar galactomannan polymers include but are not limited to tara gum (3 parts mannose/1 part galactose), locust bean or carob (4 parts mannose/1 part galactose), and cassia gum (5 parts mannose/1 part galactose). When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

A potential side reaction that may occur during the quaternization reaction of a cationic polymer production process is the formation of trimethylamine (TMA). While not intending to be limited by theory, the presence of TMA as an impurity in a cationic polymer containing composition at a pH greater than 6.8 may be found to be the source of an amine off-odor or fishy off-odor. It has surprisingly been discovered that pH has a significant effect on the level of TMA evolved into the headspace of the composition—in particular, the level of TMA in the headspace increases as the pH increases. Headspace is commonly referred to as the volume above a liquid or solid in a closed container. In turn, the level of amine off-odor can be found to be proportional to the level of TMA present in the headspace. Additionally, it has been discovered that it is possible to reverse the TMA evolution into the headspace by lowering the pH of the composition, as demonstrated and discussed in U.S. application Ser. No. 11/216,520, filed Aug. 31, 2005 on pages 22-26 and incorporated by reference herein.

Therefore, in order to produce an acceptable composition having a pH of greater than 6.8, which comprises a cationic polymer, with low to no amine off-odor, it has been discovered that it may be necessary to use a cationic polymer which contains from no detectable TMA to low levels of TMA. Levels of TMA from a cationic polymer can be measured using the method as demonstrated and discussed in U.S. application Ser. No. 11/216,520, filed Aug. 31, 2005 on pages 22-26 and incorporated by reference herein.

It has been discovered that compositions comprising cationic polymers which have levels of TMA, as measured, for example, in the method described above, below 45 ppm, preferably below 25 ppm, more preferably below 17 ppm, have no amine off-odor to low amine off-odor which has been found to be acceptable.

2. Nonionic Polymers

Polyalkylene glycols having a molecular weight of more than about 1000 are useful herein. Useful are those having the following general formula:

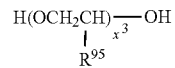

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2, 000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

3. Conditioning Agents

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

In an embodiment of the present invention, one or more conditioning agents are present from about 0.01% to about 10%, preferably from about 0.1% to about 8%, more preferably from about 0.2% to about 4%, by weight of the composition.

The conditioning agents may be present in the dispersed gel network phase or may be added to the final shampoo composition as a separate component.

1. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a volume average particle diameter ranging from about 0.01 µm to about 50 µm, as measured using the Horiba LA-910 Particle Size Analyzer. The Horiba LA-910 instrument uses the principles of low-angle Fraunhofer Diffraction and Light Scattering to measure the particle size and distribution in a dilute solution of particles. For small particle application to hair, the volume average particle diameters typically range from about 0.01 µm to about 4 µm, preferably from about 0.01 µm to about 2 µm, more preferably from about 0.01 µm to about 0.5 µm. For larger particle application to hair, the volume average particle diameters typically range from about 4 µm to about 50 µm, preferably from about 6 µm to about 40 µm, and more preferably from about 10 µm to about 35 µm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

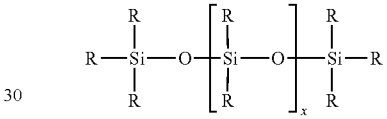

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

b. Amino and Cationic Silicones.

Cationic silicone fluids suitable for use in the compositions of the present invention include, but are not limited to, those which conform to the general formula (V):

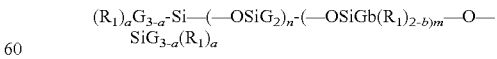

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 499; m is an integer from 1 to 2,000, preferably from 1 to 10; the sum of n and m is a number from 1 to 2,000, preferably from 50 to 500; $R_1$ is a monovalent radical conforming to the general formula CqH$_{2q}$L, wherein q is an integer having a value from 2 to 8 and L is selected from the following groups:

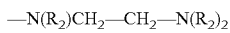

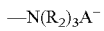

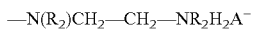

wherein R$_2$ is hydrogen, phenyl, benzyl, or a saturated hydrocarbon radical, preferably an alkyl radical from about C$_1$ to about C$_{20}$, and A$^-$ is a halide ion.

An especially preferred cationic silicone corresponding to formula (V) is the polymer known as "trimethylsilylamodimethicone", which is shown below in formula (VI):

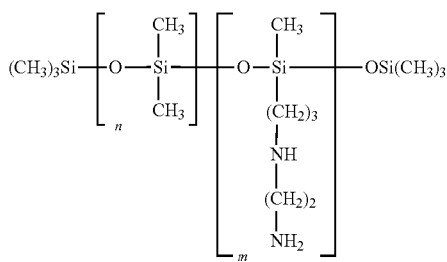

Other silicone cationic polymers which may be used in the compositions of the present invention are represented by the general formula (VII):

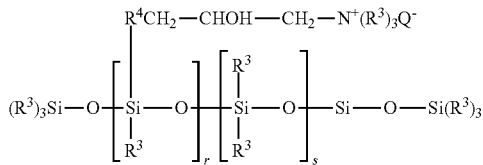

wherein R$^3$ is a monovalent hydrocarbon radical from C$_1$ to C$_{18}$, preferably an alkyl or alkenyl radical, such as methyl; R$^4$ is a hydrocarbon radical, preferably a C$_1$ to C$_{18}$ alkylene radical or a C$_{10}$ to C$_{18}$ alkyleneoxy radical, more preferably a C$_1$ to C$_8$ alkyleneoxy radical; Q$^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

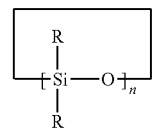

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably C$_1$-C$_4$ alkyl (more preferably methyl), hydroxy, or C$_1$-C$_4$ alkylamino (especially —R$^1$NHR$^2$NH2 wherein each R$^1$ and R$^2$ independently is a C$_1$-C$_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

e. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the compositions of the present invention may also comprise from about 0.05% to about 3%, preferably from about 0.08% to about 1.5%, more preferably from about 0.1% to about 1%, of at least one organic conditioning oil as the conditioning agent, either alone or in combination with other conditioning agents, such as the silicones (described herein).

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. The concentration of such hydrocarbon oils in the composition preferably range from about 0.05% to about 20%, more preferably from about 0.08% to about 1.5%, and even more preferably from about 0.1% to about 1%.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

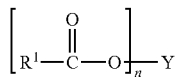

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

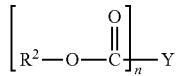

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

4. Additional Components

The compositions of the present invention may further include a variety of additional useful components. Preferred additional components include those discussed below:

1. Other Anti-Microbial Actives

The compositions of the present invention may further include one or more anti-fungal or anti-microbial actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d. Keratolytic Agents

The present invention may further comprise one or more keratolytic agents such as Salicylic Acid.

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

2. Hair Loss Prevention and Hair Growth Agent

The present invention may further comprise materials useful for hair loss prevention and hair growth stimulants or agents. Examples of such agents are Anti-Androgens such as Propecia, Dutasteride, RU5884; Anti-Inflammatories such as Glucocortisoids, Macrolides, Macrolides; Anti-Microbials such as Zinc pyrithione, Ketoconazole, Acne Treatments; Immunosuppressives such as FK-506, Cyclosporin; Vasodilators such as minoxidil, Aminexile and combinations thereof.

3. Sensates

The present invention may further comprise topical sensate materials such as terpenes, vanilloids, alkyl amides, natural extracts and combinations thereof, as demonstrated and disclosed in U.S. application Ser. No. 11/216,520, filed Aug. 31, 2005 on page 39 and incorporated by reference herein.

4. Humectant

The compositions of the present invention may contain a humectant. The humectants herein are selected from the group consisting of polyhydric alcohols, water soluble alkoxylated nonionic polymers, and mixtures thereof, as demonstrated and disclosed in U.S. application Ser. No. 11/216,520, filed Aug. 31, 2005 on pages 39-40 and incorporated by reference herein. The humectants, when used herein, are preferably used at levels of from about 0.1% to about 20%, more preferably from about 0.5% to about 5%.

5. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%. Suspending agents useful herein include anionic polymers and nonionic polymers, commercially available viscosity modifiers, and crystalline suspending agents which can be categorized as acyl derivatives, long chain amine oxides, and mixtures thereof. Suspending agents useful herein are further demonstrated and disclosed in U.S. application Ser. No. 11/216,520, filed Aug. 31, 2005 on pages 40-42 and incorporated by reference herein.

6. Other Optional Components

The compositions of the present invention may contain also vitamins and amino acids, pigment material, antimicrobial agents which are useful as cosmetic biocides and antidandruff agents including: water soluble components such as piroctone olamine, water insoluble components such as 3,4,4'-trichlorocarbanilide (triclocarban), triclosan, chelating agents, as demonstrated and disclosed in U.S. application Ser. No. 11/216,520, filed Aug. 31, 2005, on page 42 and incorporated by reference herein.

J. Coordinating Compound Having a log Zn Binding Constant

In an embodiment of the present invention, the composition further comprises a coordinating compound with a Log Zn binding constant in a range sufficient to maintain zinc bioavailability, as demonstrated and disclosed in U.S. application Ser. No. 11/216,520, filed Aug. 31, 2005 on pages 42-43 and incorporated by reference herein.

K. pH

Preferably, the pH of the present invention may be greater than about 6.5, further wherein the pH is greater than about 6.8. Further, the pH of the present invention may be in a range from about 6.5 to about 12, preferably from about 6.8 to about 10, more preferably from about 6.8 to about 9, and even more preferably from about 6.8 to about 8.5.

L. Method For Assessment of Zinc Lability in Zinc-Containing Products

Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Zinc lability is assessed by combining a diluted zinc-containing solution or dispersion with the metallochromic dye xylenol orange (XO) and measurement of the degree of color change under specified conditions. The magnitude of color formation is proportional to the level of labile zinc. The procedure developed has been optimized for aqueous surfactant formulations but may be adapted to other physical product forms as well.

A spectrophotometer is used to quantify the color change at 572 nm, the wavelength of optimum color change for XO. The spectrophotometer is set to zero absorbance at 572 nm utilizing a product control as close in composition to the test product except excluding the potentially labile form of zinc. The control and test products are then treated identically as follows. A 5011 product sample is dispensed into a jar and 95 ml of deaerated, distilled water are added and stirred. 5 mL of a 23 mg/mL xylenol orange stock solution at pH 5.0 is pipetted into the sample jar; this is considered time 0. The pH is then adjusted to 5.50±0.01 using dilute HCl or NaOH. After 10.0 minutes, a portion of the sample is filtered (0.45μ) and the absorbance measured at 572 nm. The measured absorbance is then compared to a separately measured control to determine the relative zinc lability (zero TO 100%). The 100% lability control is prepared in a matrix similar to the test products but utilizing a soluble zinc material (such as zinc sulfate) incorporated at an equivalent level on a zinc basis. The absorbance of the 100% lability control is measured as above for the test materials. The relative zinc lability is preferably greater than about 15%, more preferably greater than about 20%, and even more preferably greater than about 25%.

Using this methodology, the below examples demonstrate a material (basic zinc carbonate) that has intrinsically high lability in an anionic surfactant system compared to one (ZnO) with low intrinsic lability.

|  | Relative Zinc Lability (%) In Water | Relative Zinc Lability (%) In Simple Surfactant System[1] | Lability Benefit |
|---|---|---|---|
| Zinc Oxide | 86.3 | 1.5 | NO |
| Basic zinc carbonate | 100 | 37 | YES |

[1]Simple surfactant system: 6% sodium lauryl sulfate

M. Particle Size Determination Method

Particle size analyses on zinc oxide and hydrozincite raw materials as demonstrated and disclosed in U.S. application Ser. No. 11/216,520, filed Aug. 31, 2005 on pages 44-45 are incorporated by reference herein.

N. Surface Area Methodology

Surface area analysis as demonstrated and disclosed in U.S. application Ser. No. 11/216,520, filed Aug. 31, 2005 on page 45 are incorporated by reference herein.

O. Methods of Use

The compositions of the present invention may be used in direct application to the skin or in a conventional manner for cleansing skin and hair and controlling microbial infection (including fungal, viral, or bacterial infections) on the skin or scalp. The compositions herein are useful for cleansing the hair and scalp, and other areas of the body such as underarm, feet, and groin areas and for any other area of skin in need of treatment. The present invention may be used for treating or cleansing of the skin or hair of animals as well. An effective amount of the composition, typically from about 1 g to about 50 g, preferably from about 1 g to about 20 g of the composition, for cleansing hair, skin or other area of the body, is topically applied to the hair, skin or other area that has preferably been wetted, generally with water, and then rinsed off. Application to the hair typically includes working the shampoo composition through the hair.

A further embodiment of the present invention comprises a method of treating athlete's foot, microbial infections, improving the appearance of a scalp, fungal infections, diaper dermatitis, tinea capitis, yeast infections and candidiasis, each comprising the use of the composition according to the present invention.

Additional methods for providing anti-microbial (i.e. antidandruff) efficacy as demonstrated and disclosed in U.S. application Ser. No. 11/216,520, filed Aug. 31, 2005 on pages 46-47 are incorporated by reference herein.

P. Examples

The following examples further describe and demonstrate the preferred embodiments within the scope of the present invention. The examples are given solely for the purpose of illustration, and are not to be construed as limitations of the present invention since many variations thereof are possible without departing from its scope.

Process of Making a Shampoo Composition

An aspect of the invention relates to a process of making a shampoo composition of the present invention. The process of making a shampoo composition comprises (a) combining a fatty amphiphile, a secondary surfactant, and water at a temperature sufficient to allow partitioning of the secondary surfactant and the water into the fatty amphiphile to form a pre-mix; (b) cooling the pre-mix below the chain melt temperature of the fatty amphiphile to form a gel network; (c) adding the gel network to one or more detersive surfactants and an aqueous carrier to form a shampoo composition, d) adding the particulate zinc material, the zinc pyrithione and other embodiments, such process suitable for providing an antimicrobial composition provided that the resulting composition provides the excellent antimicrobial benefits described herein. e) adjusting the pH of the shampoo composition to a pH greater than about 6.5.

As discussed above, in one embodiment of the present invention, the gel network component is prepared as a separate pre-mix, which, after being cooled, is subsequently incorporated with the other components of the shampoo composition. More specifically, the gel network component of the present invention may be prepared by heating the fatty amphiphile, the secondary surfactant, and water to a temperature of at least about 3 deg C. higher than the melting point of the highest melting-point material in the gel network phase, and mixing. This mixture is cooled to a level in the range of about 27° C. to about 35° C. by, for example, passing the mixture through a heat exchanger. As a result of this cooling step, the fatty amphiphile and the secondary surfactant crystallize to form a crystalline gel network.

Alternative methods of preparing the gel network component include sonication and/or milling of the fatty amphiphile, the secondary surfactant, and water, while these components are heated, to reduce the particle size of the melted fatty amphiphile phase. This results in an increase in surface area of the fatty amphiphile phase, which allows the secondary surfactant and the water to swell the fatty amphiphile phase. Another suitable variation in preparing the gel network includes heating and mixing the fatty amphiphile and the secondary surfactant first, and then adding that mixture to the water.

Methods for preparing the antidandruff and other shampoo embodiments of the present invention include conventional formulation and mixing techniques. A method such as that described in U.S. Pat. No. 5,837,661, could be employed, wherein the antimicrobial agent of the present invention would typically be added in the same step as the silicone premix is added in the U.S. Pat. No. 5,837,661 description.

NON-LIMITING EXAMPLES

The shampoo compositions illustrated in the following examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following examples are prepared by conventional formulation and mixing methods, an example of which is set forth herein below. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, about 20% of the water is heated to a temperature above the melt point of the highest melting-point material in the gel network premix. In a non-limiting example, the temperature will typically fall within a range of about 65° C. to about 90° C. The gel network component of the present invention may be prepared by heating the fatty amphiphile, the secondary surfactant, and water to a temperature of at least about 3 deg C. higher than the melting point of the highest melting-point material in the gel network phase, and mixing. After incorporation, this mixture is passed through a mill and heat exchanger where it is cooled to about 35° C. As a result of this cooling step, the fatty amphiphile, the secondary surfactant, and the water form a crystalline gel network.

For mixtures of different fatty amphiphiles, it may be beneficial to pre-mix the fatty amphiphile materials before incorporation into the water. This can be done by co-melting the different fatty amphiphiles together and utilizing this melt or cooling into a solid phase and incorporating this into the heated water along with the secondary surfactant. Another variation could be to co-melt the one or more fatty amphiphiles and the secondary surfactant before incorporation into the water. Some gel network compositions with chain melt temperatures between about 27° C. to about 35° C. will need to be cooled below 27° C. to ensure the lamellar phase structure is frozen.

Gel Network Pre-Mix Examples

The following Examples illustrate specific embodiments of the gel network pre-mix, prior to its incorporation with the detersive surfactant, the antimicrobials, and other components of the final shampoo composition of the present invention. It is intended that each of the following gel network pre-mix examples could be incorporated as a dispersed phase into a shampoo composition according to the present invention.

| Ingredient | 1 | 2 | 3 | 4 | 5 | 6 |
|---|---|---|---|---|---|---|
| Water | 88.55% | 88.55% | 88.55% | 88.55% | 88.55% | 88.55% |
| Behenamidopropyl dimethylamine, Incromine BB (2) | 8.58% | | | | | |
| Glyceryl distearate (1) | | 8.58% | | | | |
| Glyceryl hydroxystearate (1) | | | 8.58% | | | |
| Glyceryl palmitate (1) | | | | 8.58% | | |
| Glyceryl stearate, Glyceryl Stearate Pure (1) | | | | | 8.58% | |
| Oleamide, Croadmide VRX Bead (2) | | | | | | 8.58% |
| Behenyltrimethylammonium chloride, Varisoft BT-85 (4) | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% |

| Ingredient | 7 | 8 | 9 | 10 | 11 | 12 | 13 |
|---|---|---|---|---|---|---|---|
| Water | 88.55% | 88.55% | 88.55% | 88.55% | 88.55% | 88.55% | 88.55% |
| PEG-2 Stearate (1) | 8.58% | | | | | | |
| PEG-5 Glyceryl stearate (1) | | 8.58% | | | | | |
| PEG-6 Stearate (1) | | | 8.58% | | | | |
| SEFA Stearate, Sefose-1618H (3) | | | | 8.58% | | | |
| Sorbitan palmitate (1) | | | | | 8.58% | | |
| Sorbitan stearate, Crill 3 NF (2) | | | | | | 8.58% | |
| Sorbitan stearate (1) | | | | | | | 8.58% |
| Behenyltrimethylammonium chloride, Varisoft BT-85 (4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 14 | 15 | 16 | 17 | 18 | 19 |
|---|---|---|---|---|---|---|
| Water | 88.55% | 88.55% | 88.55% | 88.78% | 88.55% | 88.55% |
| Glyceryl palmitate (1) | | | | | | 4.29% |
| Glyceryl stearate, Glyceryl Stearate Pure (1) | | | | | | 4.29% |
| Sorbitan tristearate (1) | 8.58% | | | | | |
| Stearamide MEA-stearate (1) | | 8.58% | | 9.90% | | |
| Steareth-2, Volpo S-2 (2) | | | 8.58% | | | |
| Sucrose distearate, Crodesta F-10 (2) | | | | | 8.58% | |
| Behenyltrimethylammonium chloride, Varisoft BT-85 (4) | 2.84% | 2.84% | 2.84% | 1.29% | 2.84% | 2.84% |
| 5-Chloro-2-methyl-4-isothiazolin-3-one, Kathon CG | 0.03% | 0.03% | 0.03% | 0.03% | 0.03% | 0.03% |

| Ingredient | 20 | 21 | 22 | 23 | 24 | 25 |
|---|---|---|---|---|---|---|
| Water | 82.75% | 82.75% | 82.75% | 82.75% | 82.75% | 82.75% |
| Behenamidopropyl dimethylamine, Incromine BB (2) | 8.58% | | | | | |
| Glyceryl distearate (1) | | 8.58% | | | | |
| Glyceryl hydroxystearate (1) | | | 8.58% | | | |
| Glyceryl palmitate (1) | | | | 8.58% | | |
| Glyceryl stearate, Glyceryl Stearate Pure (1) | | | | | 8.58% | |
| Oleamide, Crodamide VRX Bead (2) | | | | | | 8.58% |
| Sodium laureth-3 sulfate (28% Active) | 8.64% | 8.64% | 8.64% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% |

| Ingredient | 26 | 27 | 28 | 29 | 30 | 31 | 32 |
|---|---|---|---|---|---|---|---|
| Water | 82.75% | 82.75% | 82.75% | 82.75% | 82.75% | 82.75% | 82.75% |
| PEG-2 Stearate (1) | 8.58% | | | | | | |
| PEG-5 Glyceryl stearate (1) | | 8.58% | | | | | |
| PEG-6 Stearate (1) | | | 8.58% | | | | |

-continued

| Ingredient | | | | | | | |
|---|---|---|---|---|---|---|---|
| SEFA Stearate, Sefose-1618H (3) | | | | 8.58% | | | |
| Sorbitan palmitate (1) | | | | | 8.58% | | |
| Sorbitan stearate, Crill 3 NF (2) | | | | | | 8.58% | |
| Sorbitan stearate (1) | | | | | | | 8.58% |
| Sodium laureth-3 sulfate (28% Active) | 8.64% | 8.64% | 8.64% | 8.64% | 8.64% | 8.64% | 8.64% |
| 5-Chloro-2-methyl-4-isothiazotin-3-one, Kathon CG | 0.03% | 0.03% | 0.03% | 0.03% | 0.03% | 0.03% | 0.03% |

| Ingredient | 33 | 34 | 35 | 36 | 37 | 38 | 39 |
|---|---|---|---|---|---|---|---|
| Water | 82.75% | 82.75% | 82.75% | 86.14% | 82.75% | 82.585% | 82.75% |
| Cetyl Alcohol | | | | 3.46% | | 3.07% | |
| Cocamine oxide | | | | | | | 4.30% |
| Glyceryl distearate (1) | | | | | | | |
| Sorbitan tristearate (1) | 8.58% | | | | | | |
| Steary Alcohol | | | | 6.44% | | 5.53% | |
| Stearamide MEA-stearate (1) | | 8.58% | | | | | |
| Steareth-2, Volpa S-2 (2) | | | 8.58% | | | | |
| Sucrose distearate, Crodesta F-10 (2) | | | | | 8.58% | | 4.28% |
| Sodium laureth-3 sulfate (28% Active) | 8.64% | 8.64% | 8.64% | 3.93% | 8.64% | 8.78% | 8.64% |
| 5-Chloro-2-methyl-4-isothiazolin-3-one, Kathon CG | 0.03% | 0.03% | 0.03% | 0.03% | 0.03% | 0.03% | 0.03% |

| Ingredient | 40 | 41 | 42 | 43 | 44 | 45 | 46 |
|---|---|---|---|---|---|---|---|
| Water | 88.78% | 88.78% | 88.78% | 88.78% | 88.78% | 88.78% | 88.78% |
| Behenamidopropyl dimethylamine, Incromine BB (2) | 9.90% | | | | | | |
| Glyceryl distearate (1) | | 9.90% | | | | | |
| Glyceryl hydroxystearate (1) | | | 9.90% | | | | |
| Glyceryl stearate, Glyceryl Stearate Pure (1) | | | | 9.90% | | | |
| PEG-2 Stearate (1) | | | | | 9.90% | | |
| PEG-6 Stearate (1) | | | | | | 9.90% | |
| Sorbitan stearate, Crill 3 NF (2) | | | | | | | 9.90% |
| Behenyltrimethylammonium chloride, Varisoft BT-85 (2) | 1.29% | 1.29% | 1.29% | 1.29% | 1.29% | 1.29% | 1.29% |
| 5-Chloro-2-methyl-4-isothiazolin-3-one, Kathon CG | 0.03% | 0.03% | 0.03% | 0.03% | 0.03% | 0.03% | 0.03% |

| Ingredient | 47 | 48 | 49 | 50 | 51 |
|---|---|---|---|---|---|
| Water | 86.14% | 86.14% | 86.14% | 86.14% | 86.14% |
| Glyceryl distearate (1) | 9.90% | | | | 4.950% |
| Glyceryl stearate, Glyceryl Stearate Pure (1) | | 9.90% | | | |
| PEG-2 Stearate (1) | | | 9.90% | | 4.950% |
| Steareth-2, Volpo S-2 (2) | | | | 9.90% | |
| Sodium laureth-3 sulfate (28% Active) | 3.93% | 3.93% | 3.93% | 3.93% | 3.93% |
| 5-Chloro-2-methyl-4-isothiazolin-3-one, Kathon CG | 0.03% | 0.03% | 0.03% | 0.03% | 0.03% |

| Ingredient | 52 | 53 | 54 | 55 | 56 | 57 | 58 |
|---|---|---|---|---|---|---|---|
| Water | 87.13% | 82.13% | 77.13% | 72.13% | 67.13% | 77.13% | 77.13% |
| Cetyl Alcohol | 3.50% | 5.25% | 7.00% | 8.75% | 10.50% | 7.00% | 7.00% |
| Glyceryl palmitate (1) | | | | | | | 6.50% |
| Oleyl Alcohol | | | | | | 1.00% | |
| Sorbitan stearate (1) | | | | | | 6.50% | |
| Stearyl Alcohol | 6.50% | 9.75% | 13.00% | 16.25% | 19.50% | 5.50% | 6.50% |
| Behenyltrimethylammonium chloride, Varisoft BT-85 (4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 59 | 60 | 61 | 62 | 63 | 64 |
|---|---|---|---|---|---|---|
| Water | 86.14% | 82.75% | 72.60% | 72.60% | 82.75% | 80.40% |
| Behenyl Alcohol | | | | 7.87% | | 7.87% |
| Cetyl Alcohol | 3.46% | 4.18% | 5.62% | | | |
| Glyceryl distearate (1) | | | | | 4.30% | |
| Steary Alcohol | 6.44% | 7.52% | 10.12% | 7.87% | | 7.87% |
| Steareth-2, Volpa S-2 (2) | | | | | 8.64% | |
| Sodium laureth-3 sulfate (28% Active) | 3.93% | 4.64% | 11.63% | 11.63% | | |

-continued

| | | | | | | |
|---|---|---|---|---|---|---|
| Behenyltrimethylammonium chloride, Varisoft BT-85 (4) | | | | | | 3.83% |
| 5-Chloro-2-methyl-4-isothiazolin-3-one, Kathon CG | 0.03% | 0.03% | 0.03% | 0.03% | 0.03% | 0.03% |

(1) available from A&E Connock
(2) available from Croda Chemicals
(3) available from P&G Chemicals
(4) available Goldschmidt Chemical

Preparation of Final Shampoo Compositions

To prepare the final shampoo composition, first, a surfactant solution pre-mix is formed. To prepare this surfactant solution pre-mix, about 6% to about 9% of sodium laureth-3 sulfate, cationic polymers, and about 0% to about 5% of water are added to a jacketed mix tank and heated to about 74° C. with agitation. Ethylene glycol distearate (EGDS) and other cosurfactants (where applicable), and any additional materials that require heat for incorporation/melting, are then added to the mixing vessel and melted. After the EGDS is well dispersed (e.g., after about 10 minutes), preservative is added and mixed into the surfactant solution. This mixture is passed through a mill and heat exchanger where it is cooled to about 35° C. and collected in a finishing tank. As a result of this cooling step, the EGDS crystallizes to form a waxy crystalline suspension. The mixture of these components is the surfactant solution pre-mix.

Next, the surfactant solution pre-mix and the gel network pre-mix, which is prepared as described above, are mixed together. Then, basic Zinc Carbonate or other zinc-containing layered material could be added to a premix of surfactants or water with or without the aid of a dispersing agent via conventional powder incorporation and mixing techniques and then into the final mix. The pyrithione or the polyvalent metal salt of the pyrithione is added into the final mix. Product pH is adjusted, using an acid such as hydrochloric acid, to an acceptable pH. The remainder of the surfactants, other anti-dandruff actives, perfume, dimethicone, sodium chloride or sodium xylene sulfonate for viscosity adjustment, and the remainder of the water are added with ample agitation to ensure a homogeneous mixture. This mixture is the final shampoo composition which comprises as dispersed phases the gel network pre-mix and the particulate zinc material.

Preferred viscosities of the final shampoo composition according to the present invention range from about 5000 to about 15,000 centipoise at 27° C., as measured by a Wells-Brookfield model RVTDCP viscometer using a CP-41 cone and plate at 2/s at 3 minutes.

Shampoo Examples

The following Examples illustrate specific embodiments of the final shampoo composition of the present invention, which respectively comprise select above-exemplified gel network pre-mixes as a dispersed phase.

| Components | Example 1 | Example 2 | Example 3 | Example 4 | Example 5 | Example 6 | Example 7 | Example 8 | Example 9 |
|---|---|---|---|---|---|---|---|---|---|
| Sodium Laureth Sulfate | 10.00 | 10.00 | 10.00 | 10.00 | | 10.00 | 10.00 | 10.00 | 10.00 |
| Sodium Lauryl Sulfate | 6.00 | 6.00 | 6.00 | 6.00 | 2.00 | 6.00 | 6.00 | 6.00 | 6.00 |
| Decyl Glucoside | | | | | 10.00 | | | | |
| EGDS | 1.50 | 1.50 | 1.50 | 1.50 | 1.50 | 1.50 | 1.50 | 1.50 | 1.50 |
| CMEA | 0.800 | 1.60 | 0.800 | 1.600 | 0.800 | 1.600 | 0.800 | 0.800 | 0.800 |
| Cetyl Alcohol | 0.600 | 0.600 | 0.600 | 0.600 | 0.600 | 0.600 | 0.600 | 0.600 | 0.600 |
| Guar Hydroxy Propyl Trimonium Chloride (1) | 0.500 | 0.500 | 0.500 | 0.500 | 0.500 | 0.500 | 0.500 | 0.500 | 0.500 |
| Any one of Gel networks 1–37 | 27.27 | 27.27 | 27.27 | 27.27 | | | 27.27 | | |
| Gel network 61 | | | | | | 17.15 | | | |
| Gel network 63 | | | | | 6.72 | | | | |
| Gel network 60 | | | | | | | | 41.02 | |
| Gel network 64 | | | | | | | | | 17.15 |
| Dimethicone (2) | 0.85 | 0.85 | 0.85 | 0.85 | 0.85 | 0.85 | 0.85 | 0.85 | 0.85 |
| ZPT (3) | 1.00 | 1.00 | 1.00 | 1.00 | 1.00 | 1.00 | 1.00 | 1.50 | 1.75 |
| Basic Zinc Carbonate (4) | | | | | 1.61 | 1.61 | 3.22 | 1.61 | 1.61 |
| Zinc Hydroxy Sulfate (5) | 2.00 | | | | | | | | |
| Zinc Hydroxy Nitrate (5) | | 1.88 | | | | | | | |
| Zinc Hydroxy Chloride (5) | | | 1.63 | | | | | | |
| Zinc Hydroxy Lauryl Sulfate (5) | | | | 2.40 | | | | | |
| Hydrochloric Acid (6) | 0.42 | 0.42 | 0.42 | 0.42 | 0.42 | 0.42 | 0.42 | 0.42 | 0.42 |

-continued

| Components | Example 1 | Example 2 | Example 3 | Example 4 | Example 5 | Example 6 | Example 7 | Example 8 | Example 9 |
|---|---|---|---|---|---|---|---|---|---|
| Magnesium Sulfate | 0.28 | 0.28 | 0.28 | 0.28 | 0.28 | 0.28 | 0.28 | 0.28 | 0.28 |
| Sodium Chloride | 0.800 | 0.800 | 0.800 | 0.800 | 0.800 | 0.800 | 0.800 | 0.800 | 0.800 |
| Sodium Xylenesulfonate | | | | | | | | | |
| Perfume | 0.750 | 0.750 | 0.750 | 0.750 | 0.750 | 0.750 | 0.750 | 0.750 | 0.750 |
| Sodium Benzoate | 0.250 | 0.250 | 0.250 | 0.250 | 0.250 | 0.250 | 0.250 | 0.250 | 0.250 |
| Kathon | 0.0008 | 0.0008 | 0.0008 | 0.0008 | 0.0008 | 0.0008 | 0.0008 | 0.0008 | 0.0008 |
| Benzyl Alcohol | 0.0225 | 0.0225 | 0.0225 | 0.0225 | 0.0225 | 0.0225 | 0.0225 | 0.0225 | 0.0225 |
| Water | Q.S. | Q.S. | Q.S. | Q.S. | Q.S. | Q.S. | Q.S. | Q.S. | Q.S. |

(1) Guar having a molecular weight of about 400,000, and having a charge density of about 0.84 meq/g, available from Aqualon.
(2) Viscasil 330M available from General Electric Silicones
(3) ZPT having an average particle size of about 2.5 μm, available from Arch/Olin.
(4) Basic Zinc Carbonate Available from Bruggemann Chemical
(5) Materials made by reported methods in Lagaly, G.: et al. Inorg. Chem 3, 32 1209–1215 & Morioka, H; et al. Inorg Chem. 1999, 38, 4211–4216.
(6) 6N HCl, avail. From J.T. Baker, adjustable to achieve target pH

| Ingredient | 10 | 11 | 12 | 13 | 14 | 15 | 16 | 17 | 18 | 19 |
|---|---|---|---|---|---|---|---|---|---|---|
| Sodium Laureth Sulfate | 10.00 | 10.00 | 7.65 | 10.00 | 10.00 | 7.65 | 10.00 | 10.00 | 6.00 | 10.00 |
| Sodium Lauryl Sulfate | 1.5 | 6.00 | 6.35 | 6.00 | 1.5 | 6.35 | 6.00 | 1.5 | 10.00 | 6.00 |
| Cocamidopropyl betaine | 2.00 | | | 2.00 | 2.00 | | | 2.00 | | |
| Cocamide MEA | | 1.60 | | | | | 1.60 | | 1.60 | 1.60 |
| Cetyl alcohol | | 0.60 | | | | | 0.60 | | 0.60 | 0.60 |
| Gel Networks 38 | 27.27 | 13.64 | 27.27 | | 13.64 | 13.64 | 13.64 | | | |
| Any Gel Networks 39–59 | | | | 27.27 | | | | | 6.82 | 41.02 |
| Gel Networks 60 | | | | | | | | 27.27 | | |
| Zinc Pyrithione | 1.00 | 1.00 | 1.00 | 2.00 | 1.00 | 1.00 | 1.00 | 1.00 | 0.5 | 4.00 |
| Basic Zinc Carbonate | 1.6 | 1.6 | 1.6 | 1.6 | 1.6 | 1.6 | 1.6 | 1.6 | 0.8 | 3.2 |
| Magnesium sulfate | .28 | .28 | .28 | .28 | .28 | .28 | .28 | .28 | .28 | .28 |
| Benzyl alcohol | .0225 | .0225 | .0225 | .0225 | .0225 | .0225 | .0225 | .0225 | .0225 | .0225 |
| Guar Hydroxypropyl trimonium chloride (1) | | 0.50 | | | | | | | 0.50 | |
| Guar Hydroxypropyl trimonium chloride (2) | 0.40 | | 0.40 | | 0.40 | 0.40 | 0.40 | 0.20 | | |
| Polyquaterium-10 (3) | | | | 0.10 | | | | | | |
| Polyquaterium-10 (4) | | | | | | | | | | 0.40 |
| Cassia polymer (5) | | | | 0.3 | | | | | | |
| Cassia polymer (6) | | | | | | | | 0.10 | | |
| PEG-7M (7) | | | | | | | | | | 0.10 |
| Dimethicone (8) | 2.00 | 0.85 | 1.00 | | 2.00 | 1.00 | 0.85 | 2.00 | 0.50 | 0.50 |
| Dimethicone (9) | | | | 1.00 | | | | | | |
| Ethylene Glycol Distearate | 1.50 | 1.50 | 1.50 | 1.50 | 1.50 | 1.50 | 1.50 | 1.50 | 1.50 | 1.50 |
| 5-Chloro-2-methyl-4-isothiazolin-3-one, Kathon CG | 0.0006 | 0.0006 | 0.0006 | 0.0006 | 0.0006 | 0.0006 | 0.0006 | 0.0006 | 0.0006 | 0.0006 |
| Sodium Benzoate | 0.25 | 0.25 | 0.25 | 0.25 | 0.25 | 0.25 | 0.25 | 0.25 | 0.25 | 0.25 |
| Perfume | 0.40 | 0.40 | 0.40 | 0.40 | 0.40 | 0.40 | 0.40 | 0.40 | 0.40 | 0.70 |
| Benzyl alcohol | 0.0225 | 0.0225 | 0.0225 | 0.0225 | 0.0225 | 0.0225 | 0.0225 | 0.0225 | 0.0225 | 0.0225 |
| Hydrochloric acid/ Sodium Hydroxide | pH QS | pH QS | pH QS | pH QS | pH QS | pH QS | pH QS | pH QS | pH QS | pH QS |
| Sodium Chloride/ Sodium Xylene Sulfonate | Visc. QS | Visc. QS | Visc. QS | Visc. QS | Visc. QS | Visc. QS | Visc. QS | Visc. QS | Visc. QS | Visc. QS |
| Water | QS | QS | QS | QS | QS | QS | QS | QS | QS | QS |

(1) N-Hance 3269 (with Mol. W. of ~500,000 and 0.8 meq/g) available from Aqulaon/Hercules
(2) ADPP-5043HMW (with Mol.W. of ~1,200,000 and Char.Den. of 2.0 meq/g) available from Aqualon/Hercules
(3) Polymer LR30M available from Amerchol/Dow Chemical
(4) Polymer LR400 available from Amerchol/Dow Chemical
(5) Cassia galactomannan (with Mol. W. of ~200,000, charge density = 3.0 meq/g)
(6) Cassia galactomannan (with Mol. W. of ~200,000, charge density = 0.7 meq/g)
(7) Peg-7M Available from Amerchol/Dow Chemical
(8) Viscasil 330M available from General Electric Silicones
(9) DC1664 available from Dow Corning Silicones

| Ingredient | 20 | 21 | 22 | 23 | 24 | 25 | 26 |
|---|---|---|---|---|---|---|---|
| Sodium Laureth Sulfate | 10.00 | 10.00 | 10.00 | 10.00 | 10.00 | 10.00 | 10.00 |
| Sodium Lauryl Sulfate | 6.0 | 6.0 | 6.00 | 6.00 | 6.00 | 6.00 | 1.50 |
| Cocamidopropyl betaine | | | | | | | 2.00 |
| Cocamide MEA | 1.6 | 1.6 | 1.6 | 1.60 | 1.6 | 1.6 | |
| Cetyl alcohol | 0.60 | 0.60 | 0.60 | 0.60 | 0.60 | .60 | |
| Gel Networks 38 | 27.27 | 6.82 | 27.27 | | 27.27 | 6.82 | |
| Gel Networks 60 | | | | | | | 41.02 |
| Gel Networks 64 | | | | 27.27 | | | |
| Zinc Pyrithione | 1.00 | 1.0 | 1.00 | 2.00 | 1.00 | 1.00 | 0.80 |
| Basic Zinc Carbonate | 1.6 | 1.6 | 1.6 | 1.6 | 1.6 | 1.6 | 1.00 |
| Magnesium sulfate | .28 | .28 | .28 | .28 | .28 | .28 | .28 |
| Benzyl alcohol | .0225 | .0225 | .0225 | .0225 | .0225 | .0225 | .0225 |
| Guar Hydroxypropyl trimonium chloride (1) | 0.50 | 0.50 | | | | | |
| Guar Hydroxypropyl trimonium chloride (2) | | | | | 0.40 | 0.40 | 0.40 |
| Polyquaterium-10 (3) | | | 0.40 | 0.40 | | | |
| PEG-7M (4) | | | 0.10 | 0.10 | | | |
| Dimethicone (5) | 0.65 | 0.55 | 0.85 | 0.55 | 1.50 | 0.45 | 0.55 |
| Dimethicone (6) | | | | | | | |
| Ethylene Glycol Distearate | 3.00 | 1.50 | 1.50 | 1.50 | 3.00 | 1.50 | 1.50 |
| 5-Chloro-2-methyl-4-isothiazolin-3-one, Kathon CG | 0.0006 | 0.0006 | 0.0006 | 0.0006 | 0.0006 | 0.0006 | 0.0006 |
| Sodium Benzoate | 0.25 | 0.25 | 0.25 | 0.25 | 0.25 | 0.25 | 0.25 |
| Perfume | 0.40 | 0.40 | 0.40 | 0.40 | 0.40 | 0.40 | 0.40 |
| *Benzyl alcohol | 0.0225 | 0.0225 | 0.0225 | 0.0225 | 0.0225 | 0.0225 | 0.0225 |
| *Hydrochloric acid | pH QS | pH QS | pH QS | pH QS | pH QS | pH QS | pH QS |
| Sodium Chloride/ Sodium Xylene Sulfonate | Visc. QS | Visc. QS | Visc. QS | Visc. QS | Visc. QS | Visc. QS | Visc. QS |
| Water | QS | QS | QS | QS | QS | QS | QS |

(1) N-Hance 3269 (with Mol. W. of ~500,000 and 0.8 meq/g) available from Aqulaon/Hercules
(2) ADPP-5043HMW (with Mol.W. of ~1,200,000 and Char.Den. of 2.0 meq/g) available from Aqualon/Hercules
(3) Polymer LR400 available from Amerchol/Dow Chemical
(4) Peg-7M Available from Amerchol/Dow Chemical
(5) Viscasil 330M available from General Electric Silicones
(6) DC1664 available from Dow Corning Silicones 1. Topical Compositions Component amounts are listed as weight percents and exclude minor materials such as diluents, filler, and so forth. The listed formulations, therefore, comprise the listed components and any minor materials associated with such components. As used herein, "minors" refers to those optional components such as preservatives, viscosity modifiers, pH modifiers, fragrances, foam boosters, and the like. As is apparent to one of ordinary skill in the art, the selection of these minors will vary depending on the physical and chemical characteristics of the particular ingredients selected to make the present invention as described herein. Other modifications can be undertaken by the skilled artisan without departing from the spirit and scope of this invention. These exemplified embodiments of the anti-microbial shampoo of the present invention provide excellent anti-microbial efficacy. In yet another embodiment of the present invention, anti-microbial conditioners, anti-microbial leave-on tonics, and anti-microbial personal cleansing compositions may comprise the present invention.

10. Other Ingredients

The present invention may, in some embodiments, further comprise additional optional components known or otherwise effective for use in hair care or personal care products. The concentration of such optional ingredients generally ranges from zero to about 25%, more typically from about 0.05% to about 20%, even more typically from about 0.1% to about 15%, by weight of the composition. Such optional components should also be physically and chemically compatible with the essential components described herein, and should not otherwise unduly impair product stability, aesthetics or performance.

Non-limiting examples of optional components for use in the present invention include anti-static agents, foam boosters, anti-dandruff agents in addition to the anti-dandruff agents described above, viscosity adjusting agents and thickeners, suspension materials (e.g. EGDS, thixins), pH adjusting agents (e.g. sodium citrate, citric acid, succinic acid, sodium succinate, sodium maleate, sodium glycolate, malic acid, glycolic acid, hydrochloric acid, sulfuric acid, sodium bicarbonate, sodium hydroxide, and sodium carbonate), preservatives (e.g. DMDM hydantoin), anti-microbial agents (e.g. triclosan or triclocarbon), dyes, organic solvents or diluents, pearlescent aids, perfumes, fatty alcohols, proteins, skin active agents, sunscreens, vitamins (such as retinoids including retinyl propionate, vitamin E such as tocopherol acetate, panthenol, and vitamin B3 compounds including niacinamide), emulsifiers, volatile carriers, select stability actives, styling polymers, organic styling polymers, silicone-grafted styling polymers, cationic spreading agents, pediculocides, foam boosters, viscosity modifiers and thickeners, polyalkylene glycols and combinations thereof.

Optional anti-static agents such as water-insoluble cationic surfactants may be used, typically in concentrations ranging from about 0.1% to about 5%, by weight of the composition. Such anti-static agents should not unduly interfere with the in-use performance and end-benefits of the anti-microbial composition; particularly, the anti-static agent should not interfere with the anionic surfactant. A specific non-limiting example of a suitable anti-static agents is tricetyl methyl ammonium chloride.

Optional foam boosters for use in the present invention described herein include fatty ester (e.g. $C_8$-$C_{22}$) mono- and di ($C_1$-$C_5$, especially $C_1$-$C_3$) alkanol amides. Specific non-limiting examples of such foam boosters include coconut monoethanolamide, coconut diethanolamide, and mixtures thereof.

Optional viscosity modifiers and thickeners may be used, typically in amounts effective for the anti-microbial compositions of the present invention to generally have an overall viscosity from about 1,000 csk to about 20,000 csk, preferably from about 3,000 csk to about 10,000 csk. Specific non-limiting examples of such viscosity modifiers and thickeners include: sodium chloride, sodium sulfate, and mixtures thereof.

Q. Other Preferred Embodiments

Other preferred embodiments of the present invention include the following:

An embodiment of the present invention, relates to the composition may be employed to treat a variety of conditions, including: athlete's foot, microbial infections, improving the appearance of a scalp, treating fungal infections, treating dandruff, treating diaper dermatitis and candidiasis, treating tinea capitis, treating yeast infections, treating onychomycosis. Preferably, such conditions are treated by applying a composition of the present invention to the affected area.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a dispersed gel network comprising:
   a) an effective amount of a particulate zinc material;
   b) from about 8% to about 30% of a detersive surfactant with an anionic functional group;
   c) an effective amount of a pyrithione or a polyvalent metal salt of a pyrithione;
   d) a pre-formed dispersed gel network phase comprising:
      i) at least 0.05% of one or more fatty amphiphiles, by weight of said shampoo composition;
      ii) at least 0.01% of one or more secondary surfactants, by weight of said shampoo composition; and
      iii) water; and
   e) at least 20% of an aqueous carrier, by weight of said shampoo composition.

2. A composition according to claim 1 wherein the pyrithione or polyvalent metal salt of pyrithione is zinc pyrithione.

3. A shampoo composition according to claim 1, wherein said fatty amphiphile is present relative to said secondary surfactant at a weight ratio of greater than 1:5 to 100:1.

4. A shampoo composition according to claim 1, wherein said fatty amphiphile is present relative to said secondary surfactant at a weight ratio of greater than 2:1 to 10:1.

5. A shampoo composition according to claim 1, wherein said fatty amphiphile is selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, and phospholipids.

6. A shampoo composition according to claim 1, wherein said pre-formed dispersed gel network phase is present in an amount from about 1% to about 60%, by weight of said shampoo composition.

7. A shampoo composition according to claim 1, wherein said secondary surfactant is selected from the group consisting of cationic surfactants, anionic surfactants, nonionic surfactants, and mixtures thereof.

8. A shampoo composition according to claim 7, wherein said cationic surfactant is selected from the group consisting of cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

9. A shampoo composition according to claim 7, wherein said anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof.

10. A shampoo composition according to claim 7, wherein said nonionic surfactant is selected from the group consisting of polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives, polyethoxylated fatty amines, alkyl polyglucosides, sugar esters, polyglyceryl fatty acid esters, alkyl polyglyceryl ethers, and mixtures thereof.

11. A composition according to claim 1 wherein the particulate zinc material has a relative zinc lability of greater than 15%.

12. A composition according to claim 1 wherein the composition comprises less than 5.5 micromoles of a zinc binding material per gram of the particulate zinc material/per $m^2$/gram surface area of the particulate zinc material.

13. A composition according to claim 12 wherein the zinc binding material is selected from the group comprising laurate, citrate, valerate, oxalate, tartrate, iodate, thiocyanate, cyanide, sulfide, pyrophosphate, phosphate and mixtures thereof.

14. A composition according to claim 13 wherein the zinc binding material is laurate.

15. A composition according to claim 2 wherein the zinc pyrithione is present from about 0.01% to about 5%.

16. A composition according to claim 1 wherein the detersive surfactant is selected from the group consisting of anionic, cationic, nonionic, amphoteric or zwitterionic.

17. A composition according to claim 16 wherein the surfactant is anionic.

18. A composition according to claim 1 wherein the pH is greater than 6.5.

19. A composition according to claim 18 wherein the pH is from about 6.8 to about 9.5.

20. A composition according to claim 19 wherein the pH is from about 6.8 to about 8.5.

21. A composition according to claim 1 wherein the particulate zinc material has a relative zinc lability of greater than 20%.

22. A composition according to claim 1 wherein the particulate zinc material has a relative zinc lability of greater than 25%.

23. A composition according to claim 1 wherein the particulate zinc material is selected from the group consisting of inorganic materials, natural zinc sources, ores, minerals, organic salts, polymeric salts, or physically adsorbed from material and mixtures thereof.

24. A composition according to claim 23 wherein the inorganic materials is selected from the group consisting of zinc aluminate, zinc carbonate, zinc oxide, calamine, zinc phosphate, zinc selenide, zinc sulfide, zinc silicates, zinc silicofluoride, zinc borate, or zinc hydroxide and zinc hydroxy sulfate, zinc-containing layered material and mixtures thereof.

25. A composition according to claim 24 the zinc-containing layered material is selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts and mixtures thereof.

26. A composition according to claim 25 wherein the zinc-containing layered material is selected from the group consisting of zinc carbonate hydroxide, hydrozincite, basic zinc carbonate and mixtures thereof.

27. A composition according to claim 26 wherein the zinc-containing layered material is hydrozincite or basic zinc carbonate.

28. A composition according to claim 27 wherein the zinc-containing layered material is basic zinc carbonate.

29. A composition according to claim 1 wherein the composition further comprises a cationic deposition polymer.

30. A composition according to claim 29 wherein the cationic polymer has a trimethylamine level of less than 45 ppm.

31. A composition according to claim 1 wherein the composition further comprises a conditioning agent.

32. A composition according to claim 31 wherein the conditioning agent is a silicone.

33. A composition according to claim 1 wherein the composition further comprises a suspending agent.

34. A composition according to claim 33 wherein the suspending agent is selected from the group consisting of crystalline suspending agent, polymeric suspending agent or mixtures thereof.

35. A composition according to claim 34 wherein the suspending agent is a crystalline suspending agent.

36. A method of treating dandruff comprising the use of the composition of claim 1.

37. A process for preparing a shampoo composition according to claim 1, said process comprising the steps of:
   a) combining a fatty amphiphile, a secondary surfactant, and water at a temperature sufficient to allow partitioning of said secondary surfactant and said water into said fatty amphiphile to form a pre-mix;
   b) cooling said pre-mix below the chain melt temperature of said fatty amphiphile to form a gel network;
   c) combining said gel network, particulate zinc material, and pyrithione or a polyvalent metal salt of a pyrithione to one or more detersive surfactants and an aqueous carrier to form a shampoo composition.

* * * * *